United States Patent
Takai et al.

(10) Patent No.: US 11,890,246 B2
(45) Date of Patent: Feb. 6, 2024

(54) MOTION TEACHING SYSTEM AND MOTION TEACHING METHOD

(71) Applicant: Advanced Telecommunications Research Institute International, Kyoto (JP)

(72) Inventors: Asuka Takai, Kyoto (JP); Tomoyuki Noda, Kyoto (JP); Giuseppe Lisi, Kyoto (JP); Tatsuya Teramae, Kyoto (JP); Jun Morimoto, Kyoto (JP); Hiroshi Imamizu, Kyoto (JP)

(73) Assignee: Advanced Telecommunications Research Institute International, Kyoto (JP)

(*) Notice: Subject to any disclaimer, the term of this patent is extended or adjusted under 35 U.S.C. 154(b) by 1230 days.

(21) Appl. No.: 16/308,409

(22) PCT Filed: Jun. 7, 2017

(86) PCT No.: PCT/JP2017/021213
§ 371 (c)(1),
(2) Date: Dec. 7, 2018

(87) PCT Pub. No.: WO2017/213202
PCT Pub. Date: Dec. 14, 2017

(65) Prior Publication Data
US 2019/0125612 A1    May 2, 2019

(30) Foreign Application Priority Data
Jun. 8, 2016  (JP) .................. 2016-114200

(51) Int. Cl.
*A61H 1/02* (2006.01)
*A63B 23/12* (2006.01)
(Continued)

(52) U.S. Cl.
CPC ............. *A61H 1/0274* (2013.01); *A61H 1/02* (2013.01); *A61H 1/0237* (2013.01); *A63B 23/04* (2013.01);
(Continued)

(58) Field of Classification Search
CPC .......................... A61H 1/0274; A61H 1/0237
See application file for complete search history.

(56) References Cited

U.S. PATENT DOCUMENTS

2006/0074822 A1    4/2006  Eda et al.
2009/0099627 A1    4/2009  Molnar et al.
(Continued)

FOREIGN PATENT DOCUMENTS

CN    104706495 A    6/2015
JP    2006-247280 A  9/2006
(Continued)

OTHER PUBLICATIONS

English translation of WO 2015052816 A1 (Year: 2015).*
(Continued)

*Primary Examiner* — Nicholas Kiswanto
*Assistant Examiner* — Christopher A Buksa
(74) *Attorney, Agent, or Firm* — Knobbe Martens Olson & Bear LLP

(57) ABSTRACT

A motor teaching system is provided with a force presentation robot for teaching motion in accordance with a predetermined motor pattern by guiding movement of a movable part of the body of a test subject, a brainwave sensor, and a computer that classifies a cerebral activity pattern into one of a plurality of classes that include motor imagery, based on a brainwave signal. The computer guides evoking contents of the test subject prior to teaching of the
(Continued)

motor pattern, such that a classification result obtained in the period of teaching the motor pattern will be the motor imagery class.

13 Claims, 22 Drawing Sheets

(51) Int. Cl.
*B25J 11/00* (2006.01)
*A63B 23/04* (2006.01)
*G06F 3/01* (2006.01)
*B25J 9/00* (2006.01)
*B25J 13/08* (2006.01)

(52) U.S. Cl.
CPC .............. *A63B 23/12* (2013.01); *B25J 9/0006* (2013.01); *B25J 11/00* (2013.01); *B25J 13/08* (2013.01); *G06F 3/01* (2013.01); *G06F 3/015* (2013.01); *A61H 2201/1659* (2013.01); *A61H 2230/105* (2013.01)

(56) References Cited

U.S. PATENT DOCUMENTS

| | | | |
|---|---|---|---|
| 2011/0071443 A1* | 3/2011 | Weisz | A61H 1/0237 601/40 |
| 2011/0218453 A1 | 9/2011 | Hirata et al. | |
| 2014/0171757 A1 | 6/2014 | Kawato et al. | |
| 2015/0196800 A1 | 7/2015 | Macri et al. | |
| 2017/0113015 A1 | 4/2017 | Kaneko | |

FOREIGN PATENT DOCUMENTS

| | | | |
|---|---|---|---|
| JP | 2011-186667 A | 9/2011 | |
| JP | 2013-099392 A | 5/2013 | |
| JP | 2014-104549 A | 6/2014 | |
| JP | 2016-013182 A | 1/2016 | |
| JP | 2016013182 A * | 1/2016 | ........... A61B 5/0476 |
| JP | 2016-054994 A | 4/2016 | |
| KR | 10-2014-0040309 A | 4/2014 | |
| KR | 101394953 B1 | 5/2014 | |
| KR | 20140063362 A | 5/2014 | |
| WO | WO 2015/052816 A1 | 4/2015 | |
| WO | WO-2015052816 A1 * | 4/2015 | ........... A61B 5/0075 |
| WO | WO 2015/152122 A1 | 10/2015 | |

OTHER PUBLICATIONS

English translation of JP 2016013182 (Year: 2016).*
Extended European Search Report, EP Patent Application No. 17810376.8, dated May 15, 2020.
Jochumsen, Mads, et al., "Comparison of spatial filters and features for the detection and classification of movement-related cortical potentials in healthy individuals and stroke patients," Journal of Neural Engineering, vol. 12, No. 5, Jul. 27, 2015.
Supplementary Partial European Search Report, European Patent Application No. 17810376.8, dated Jan. 30, 2020.
Office Action, Chinese Patent Application No. 201780035764.6, dated Jul. 16, 2020.
Geurts, et al. 2006 "Extremely randomized trees" *Mach Learn* 63: 3-42.
Reis, et al. 2014 "Methodological aspects of EEG and body dynamics measurements during motion" *Frontiers in Human Neuroscience* 8(156): 1-19.
Soekadar, et al. 2011 "ERD-Based online brain-machine interfaces (BMI) in the context of neurorehabilitation: Optimizing BMI learning and performance" *IEEE Transactions on Neural Systems and Rehabilitation Ingineering* 19(5): 542-549.
Tomioka, et al. 2006 "Adapting spatial filtering methods for nonstationary BCIs" *Workshop on Information-Based Induction Sciences*: in 6 pages.
Wojcikiewicz, et al. 2009 "Improving classification performance of BCIs by using stationary common spatial patterns and unsupervised bias adaptation" in Hybrid Artificial Intelligent Systems, ser. Lecture Notes in Computer Science. Springer Berlin Heidelberg, vol. 6679, pp. 34-41.
Wong, et al. 2012 "Can proprioceptive training improve motor learning?" *J Neurophysiol* 108: 3313-3321.
Yong, et al. 2008 "Robust common spatial patterns for EEG signal preprocessing" *30th Annual International IEEE EMBS Conference*: 2087-2090.
Office Action in European Application No. 17 810 376.8, dated May 23, 2023 (in 13 pages).

* cited by examiner

MOTION TEACHING SYSTEM AND MOTION TEACHING METHOD

TECHNICAL FIELD

The present invention relates to a motor teaching system and a motor teaching method for classifying a state of cerebral activity from a cerebral activity signal of a user and providing motor learning that depends on the classification result.

BACKGROUND ART

In teaching new motion from person to person or teaching safer and more stylish motion, a communication method is often taken that involves one person teaching another person by showing the other person how to move and moving the other person's arms and legs, for example. Furthermore, in recent years, not only person-to-person teaching but methods that involve teaching motion to a person by passively moving the person's arms and legs using an actuation system such as a robotic arm are being studied.

For example, Patent Literature 1 discloses an upper limb rehabilitation device for providing training that allows a patient to recover mobility of his or her upper limbs, the device having at least one driving means that transmits drive to an action having at least one degree of freedom out of the three degrees of freedom of a patient's wrist and conveys a mechanical sensation to the patient, and at least one functional fluid clutch that adjusts the drive of the driving means.

Also, Patent Literature 2 discloses a device that infers the motion of a patient in real time from biosignals such as brainwaves and myoelectricity, and executes rehabilitation of the patient based on the inferred motion.

On the other hand, in recent years, development is advancing not only into simple robotic arms such as disclosed in the abovementioned Patent Literatures but also into robots that support rehabilitation such as exoskeleton robots aimed at supporting motion of the upper limbs, lower limbs and trunk. For example, exoskeleton robots are used for stroke patients and the like in rehabilitation that promotes the patient's independence (see Patent Literature 3).

Patent Literature 3 discloses a configuration in which a control unit decodes the cerebral activity of a user, based on signals measured from test subjects, and controls pressure that is applied to air muscles and torque that is generated by an electric motor, in order to generate driving force for the air muscles and driving force for the electric motor so as to switch the degree of gravity compensation by an active joint, according to the decoded cerebral activity.

More generally, as a method of allowing motion to be mastered, learning such as for moving the limbs of the learner passively using a robot, instead of a sports coach or rehabilitation therapist, is called proprioceptive training.

In proprioceptive training, the learner imagines the movement of part of his or her body such as an arm or a leg, for example, and feedback on the rhythm of sensory motion is given in the form of proprioceptive afferent input from the movement of the robot. Here, "proprioceptive" refers to working on a sensory receptor that gives the position of the body and the information on motion, and "afferent" refers to transmitting stimulus and excitement from the periphery to the central nervous system. Accordingly, in the case of working with a stroke patient, for example, the patient learns motor imagery gradually during training, and, at the same time, it also becomes possible for the plasticity of nerve system to be stimulated and associated with recovery for motor control.

Robots that are used for proprioceptive training are able to perform positional control in line with a predetermined target motion, and are considered to be particularly suitable for teaching new motion. For example, there is a report on the learning effects of two-dimensional motion with a method involving both force by a robot and vision being fed back to the learner (Non-patent Literature 1). Non-patent Literature 1 reports that proprioceptive training is an effective method of motor learning, as a result of the test subjects experiencing the target motion passively, given that positional error with respect to the target action decreases, compared to only seeing the motion visually.

CITATION LIST

Patent Literature

Patent Literature 1: JP 2006-247280A
Patent Literature 2: JP 2016-54994A
Patent Literature 3: JP 2014-104549A

Non-Patent Literature

Non-patent Literature 1: Wong, Jeremy D., et al. "Can proprioceptive training improve motor learning?" Journal of Neurophysiology 108.12 (2012): 3313-3321.

SUMMARY OF INVENTION

Technical Problem

However, heretofore, the state of cerebral activity of the test subjects, when passively teaching motion, has not been taken into consideration at all. In particular, there have been no studies whatsoever in relation to what state the subject's brain should be in during motor teaching, in order to efficiently learn a motor pattern. In this regard, there is, for example, a report stating that the percentage of correct answers to questions relating to landscapes shown to the test subjects when the activity of the hippocampus that controls memory of landscapes was high compared to when the activity was low, as a result of research in relation to memory. In view of this, if the brain can be prepared in advance to be in a state suitable for a motor task before the motor task is taught, an improvement in the learning effect can be expected. To actually teach a series of motor tasks, however, takes time to implement as a teaching operation, and there have been no studies whatsoever about whether a suitable state of cerebral activity can be maintained in that teaching period.

The present invention, in one aspect, was made in consideration of such issues, and an object thereof is to provide a motor teaching system and a motor teaching method that enable motor training to be implemented on a subject, after having guided the cerebral activity of the subject into a desirable state for mastering a motor pattern.

Solution to Problem

A motor teaching system according to one aspect of the present invention is a motor teaching system for detecting cerebral activity of a subject and supporting motor training of the subject, including an operation device configured to teach motion to the subject in accordance with a predetermined motor pattern by guiding movement of a movable part of a body of the subject, a measurement device configured to acquire a cerebral activity signal, by measuring the cerebral activity of the subject, and one or a plurality of computers configured to control an operation for teaching the motor pattern by the operation device and configured to classify the cerebral activity of the subject into one of a plurality of classes including a motor imagery class by decoding the cerebral activity signal, the one or plurality of computers outputting whether the cerebral activity of the subject during a teaching period of the motor pattern is classified into the motor imagery class, as a result of decoding the cerebral activity signal acquired by the measurement device during the period in which the operation device is caused to execute the operation for teaching the motor pattern. Note that motor imagery may be referred to as "motor mental practice".

In the motor teaching system according to the above aspect, the one or plurality of computers may output evoking contents to be performed to the subject prior to teaching of the motor pattern, such that the cerebral activity of the subject during the teaching period of the motor pattern is classified into the motor imagery class.

In the motor teaching system according to the above aspect, the one or plurality of computers may instruct the subject to evoke the evoking contents, prior to teaching of the motor pattern, and instruct the operation device to start the operation for teaching the motor pattern, in response to the cerebral activity of the subject being classified into a class corresponding to the evoking contents, as a result of decoding the cerebral activity signal acquired prior to teaching of the motor pattern.

In the motor teaching system according to the above aspect, the one or plurality of computers may feed back the result of having classified the cerebral activity of the subject, prior to teaching of the motor pattern, and may not feed back the result of having classified the cerebral activity of the subject, during teaching of the motor pattern.

In the motor teaching system according to the above aspect, the one or plurality of computers may cause the operation device to execute the operation for teaching the motor pattern, in response to the cerebral activity of the subject being classified into a class corresponding to the evoking contents, as a result of decoding the cerebral activity signal acquired by the measurement device, after instructing the subject to evoke the evoking contents, change the evoking contents for instructing to the subject, in a case where the cerebral activity of the subject is classified into a class other than the motor imagery class, as a result of decoding the cerebral activity signal acquired by the measurement device, during the teaching period of the motor pattern, instruct the subject to evoke the changed evoking contents, and cause the operation device to again execute the operation for teaching the motor pattern, in response to the cerebral activity of the subject being classified into a class corresponding to the changed evoking contents, as a result of decoding the cerebral activity signal acquired by the measurement device, after instructing evoke of the changed evoking contents.

In the motor teaching system according to the above aspect, the evoking contents may be one of a rest state and a motor imagery state.

In the motor teaching system according to the above aspect, the operation device may be a force presentation device comprising a robotic arm.

In the motor teaching system according to the above aspect, the operation device may be an exoskeleton robot.

In the motor teaching system according to the above aspect, the measurement device may include a wireless headset using a dry electrode.

Also, a motor teaching method according to one aspect of the present invention is a motor teaching method for detecting cerebral activity of a subject and supporting motor training of the subject, using a system including an operation device configured to teach motion to the subject in accordance with a predetermined motor pattern by guiding movement of a movable part of a body of the subject, a measurement device configured to acquire a cerebral activity signal, by measuring the cerebral activity of the subject, and one or a plurality of computational devices, the method including a step in which the one or plurality of computational devices instruct the subject to evoke predetermined evoking contents prior to teaching of the motor pattern, such that the cerebral activity of the subject during the teaching period of the motor pattern is classified into a motor imagery class, a step in which the one or plurality of computational devices classify the cerebral activity of the subject into one of a plurality of classes including the motor imagery class, by decoding the cerebral activity signal acquired by the measurement device, and a step in which the one or plurality of computational devices cause the operation device to execute an operation for teaching the motor pattern, in response to the cerebral activity of the subject being classified into a class corresponding to the evoking contents, as a result of decoding the cerebral activity signal acquired prior to teaching of the motor pattern.

Also, a computer according to one aspect of the present invention is a computer including one or plurality of computational devices and a storage device configured to hold a program that is executed by the one or plurality of computational devices, the one or plurality of computational devices executing a step of acquiring, for each of a plurality of subjects, a spatial filter to be utilized in decoding cerebral activity of the subject, and a reproducibility of a predetermined motor pattern calculated based on a result of having performed motion reproduction of the motor pattern, after teaching the motor pattern using an operation device configured to teach motion in accordance with the motor pattern by guiding movement of a movable part of a body of the subject, a step of classifying the spatial filters of the subjects into a plurality of groups, by clustering the spatial filters of the subjects, and a step of specifying, from the plurality of groups, an optimal group to which a spatial filter of a subject with a highest degree of mastery of the motor pattern belongs, based on the reproducibility of the motor patterns of the subjects.

Also, a motor teaching system according to one aspect of the present invention is a motor teaching system for detecting cerebral activity of a subject and supporting motor training of the subject, including an operation device configured to teach motion to the subject in accordance with a predetermined motor pattern by guiding movement of a movable part of a body of the subject, a measurement device configured to acquire a cerebral activity signal, by measuring the cerebral activity of the subject, and one or plurality of computers configured to control an operation for teaching the motor pattern by the operation device and configured to classify the cerebral activity of the subject into one of a plurality of classes including a motor imagery class by decoding the cerebral activity signal, the one or plurality of computers executing a first step of acquiring, for the subject, prior to teaching of the motor pattern by the operation device, a set of a cerebral activity signal from when the motor imagery is carried out and a cerebral activity signal from when imagery other than the motor imagery is carried out, as a training data set, a second step of creating a spatial filter to be utilized in decoding the cerebral activity of the subject, based on the training data set, a third step of determining whether the created spatial filter belongs to the optimal group specified by the computer, and a fourth step of starting teaching of the motor pattern by the operation device, in a case where the created spatial filter belongs to the optimal group.

In the motor teaching system according to the above aspect, the one or plurality of computers again execute the first step, the second step and the third step, in a case where the created spatial filter does not belong to the optimal group.

In the motor teaching system according to the above aspect, a recommended class in which cerebral activity recommended during the teaching period of the motor pattern may be associated with the optimal group, and the one or plurality of computers may output evoking contents to be performed to the subject prior to teaching of the motor pattern, such that the cerebral activity of the subject during the teaching period of the motor pattern is classified into the recommended class associated with the optimal group.

Also, a motor teaching system according to one aspect of the present invention is a motor teaching system for detecting cerebral activity of a subject and supporting motor training of the subject, including an operation device configured to teach motion to the subject in accordance with a predetermined motor pattern by guiding movement of a movable part of a body of the subject, a measurement device configured to acquire a cerebral activity signal, by measuring the cerebral activity of the subject, and one or plurality of computers configured to control an operation for teaching the motor pattern by the operation device and configured to classify the cerebral activity of the subject into one of a plurality of classes including a motor imagery class by decoding the cerebral activity signal, the one or plurality of computers execute the steps of acquiring, for the subject, prior to teaching of the motor pattern by the operation device, a set of a cerebral activity signal from when the motor imagery is carried out and a cerebral activity signal from when imagery other than the motor imagery is carried out, as a training data set, creating a plurality of spatial filters for decoding the cerebral activity of the subject, based on the training data set, selecting, from the plurality of created spatial filters, a spatial filter belonging to the optimal group specified by the computer, creating a decoder configured to be utilized in decoding the cerebral activity of the subject, utilizing the selected spatial filter, and instructing the subject to perform the motor imagery, until an output of the created decoder becomes larger than a threshold.

Advantageous Effects of Invention

According to the present invention, motor training can be implemented of a subject, after having guided the cerebral activity of the subject into a desirable state for mastering a motor pattern.

DESCRIPTION OF EMBODIMENTS

Figure 1:
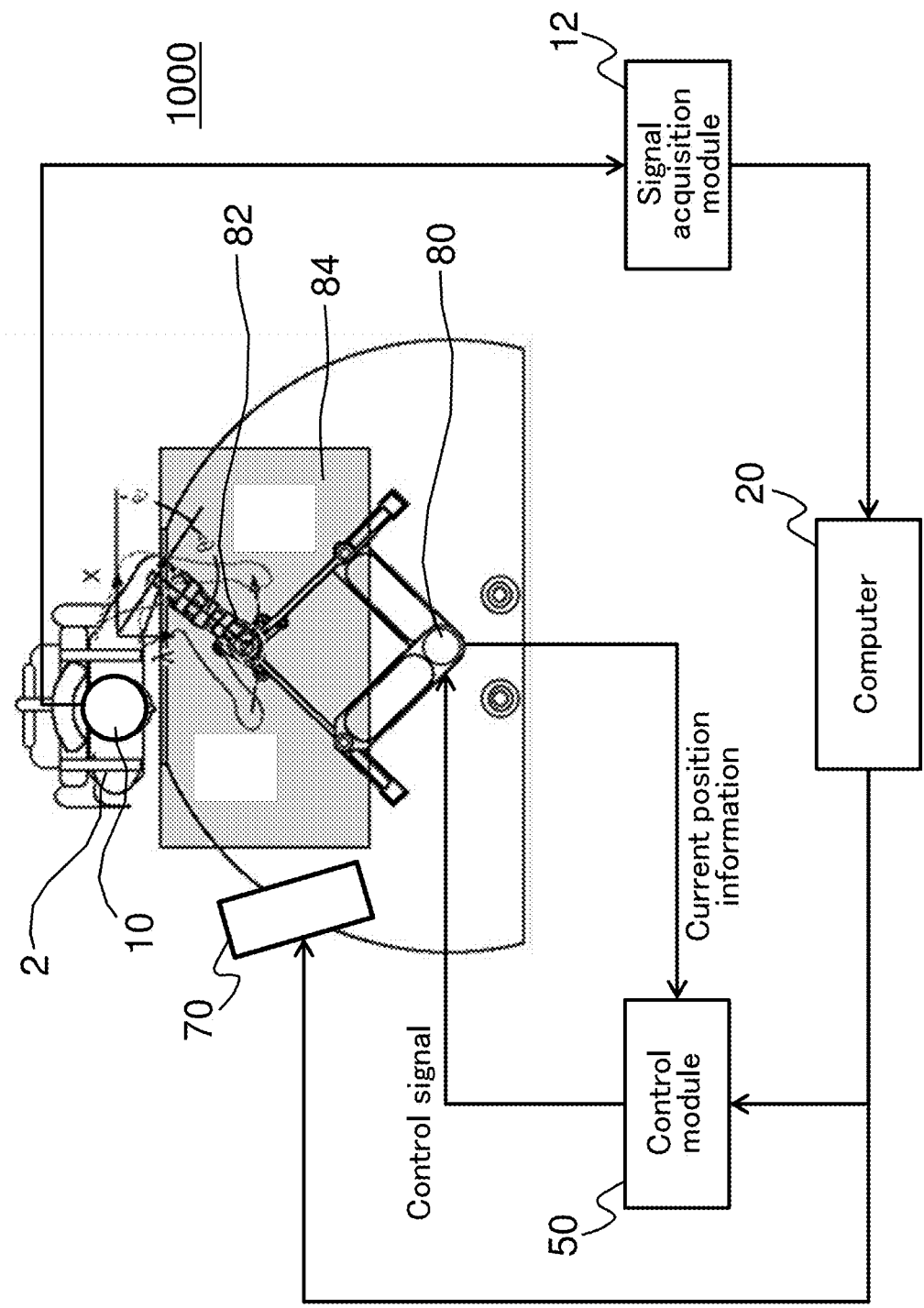
FIG. 1 schematically illustrates a configuration of a motor teaching system according to an embodiment.

Hereinafter, the respective configurations of a motor teaching system of embodiments of the present invention, a classification device that classifies patterns of cerebral activity, a motor control device that controls motor teaching operations, and an analysis device that analyzes an optimal group of cerebral activity will be described, in accordance with the diagrams. Note that, in the following embodiments, constituent elements and processing steps that are given the same reference numerals are the same or equivalent, and where unnecessary, description thereof will not be repeated.

Also, a force presentation device, in the motor teaching system, that uses a robotic arm as a robot for allowing a learner to learn motion by passively driving a movable part (e.g., upper limb, lower limb) of the learner will be described as an example. With regard to the upper limbs or the lower limbs, for example, the test subject is assumed to passively train using the force presentation device, such that the motion of at least one of the upper limbs or at least one of the lower limbs follows a predetermined motor pattern. This predetermined motor pattern may be two-dimensional or may be three-dimensional.

Note that, as the robot for implementing motor learning, an exoskeleton robot such as disclosed in the abovementioned Patent Literature 3 may be used. Also, as the actuator for driving the joints of such an exoskeleton robot, apart from an electric motor, "a pneumatic-electric hybrid actuator" such as disclosed in Patent Literature 3 may be used, as an example.

1. Exemplary Configuration of Motor Teaching System

First, an exemplary configuration of a motor teaching system 1000 according to the present embodiment will be described, using FIG. 1. FIG. 1 schematically illustrates the configuration of the motor teaching system 1000 according to the present embodiment. The motor teaching system 1000 detects the cerebral activity of a test subject 2 and supports motor training of the test subject 2. This test subject 2 is equivalent to a "subject" of the present invention.

As shown in FIG. 1, the motor teaching system 1000 according to the present embodiment is provided with a brainwave sensor 10 that is worn by the test subject 2, a signal acquisition module 12 for acquiring a signal from the brainwave sensor 10, a force presentation device 80 that is a robot for motor teaching, a control module 50 that controls the operations of the force presentation device 80, a projector 70 that performs display of various types of information, and a computer 20 that controls the operations of each device.

The brainwave sensor 10 corresponds to the "measurement device" of the present invention, and is configured to acquire cerebral activity signals (brainwave signals) by measuring the cerebral activity of the test subject 2. The type of this brainwave sensor 10 may be selected as appropriate according to the embodiment. For example, an electroencephalograph that uses a wet (gel) electrode may be utilized as the brainwave sensor 10. Also, a wireless electroencephalograph may be utilized in a dry state as the brainwave sensor 10. The present embodiment describes the wireless electroencephalograph being used in the dry state.

Such a dry wireless electroencephalograph is disclosed, for example, in Known Literature 1 (P. M. R. Reis, F. Hebenstreit, F. Gabsteiger, V. von Tscharner, and M. Lochmann, "Methodological aspects of EEG and body dynamics measurements during motion". Frontiers in human neuroscience, vol. 8, p. 156, March 2014). Note that the following embodiment describes a method utilizing a so-called electroencephalograph, as an example of a measurement method that acquires information on cerebral activity from the test subject 2. However, the present invention is not limited to such a measurement method, and other methods of measuring cerebral activity including measurement methods such as fMRI (functional Magnetic Resonance Imaging) and NIRS (Near-InfraRed Spectroscopy), for example, or a combination of other measurement methods may be used.

The signal acquisition module 12 is appropriately configured to acquire cerebral activity signals indicating the cerebral activity of the test subject 2 from various types of brainwave sensors 10 using known power supplies, amplifiers, A/D conversion circuits and the like, for example. The signal acquisition module 12 transmits the acquired cerebral activity signals to the computer 20.

The force presentation device 80 corresponds to the "operation device" of the present invention, and is configured to guide the movement of movable parts of the body of the test subject 2, and execute motor teaching in accordance with predetermined motor patterns. In the present embodiment, the force presentation device 80 is constituted as a robotic arm including a plurality of joints, arms that couple the joints, and an operation part 82 that is held by the test subject 2. The operation part 82 is a handle, for example, and is utilized for feeding back force to the test subject 2 and for allowing the test subject 2 to carry out operations when reproducing a motor pattern that has been learned.

The motor that drives the robotic arm is constituted using a servo motor, for example, and applies torque to the operation part 82. Also, the current position of the operation part 82 is detected, by a sensor which is not illustrated, and the detected current position is fed back to the control module 50 as local position information. Furthermore, the robotic arm is constituted by two arms, for example, the first arm being rotatably attached to a casing of the force presentation device 80, and the second arm being rotatably coupled via the joints. The operation part 82 is rotatably attached to the tip of another arm.

By adopting such a configuration, the operation part 82 is constituted to be displaceable on a two-dimensional plane by upper limb motion of the test subject 2. A tabular screen 84 is, however, disposed as a shielding material, slightly above the operation part 82, such that the operation part 82 is not directly visible to the test subject 2.

The control module 50 is constituted by a microcomputer, a motor driver and the like, for example, so as to control the operations of the force presentation device 80, in accordance with commands from the computer 20. The force presentation device 80 moves along the trajectory of an instructed motor pattern, according to a control signal from the control module 50, and feeds back force to the test subject 2. Also, the control module 50 monitors the current position of the operation part 82 that is held by the test subject 2, based on signals from the force presentation device 80. Note that the control module 50 may be configured to be able to measure force acting on the operation part 82. In this case, the control module 50 is able to control the force presentation device 80 to stop motor teaching, in the case where a force greater than or equal to a certain level acts on the operation part 82. Safety during motor teaching can thereby be ensured.

The projector 70 is disposed to display various types of information on the screen 84. As will be discussed later, the projector 70 is controlled by the computer 20, and transmits various types of information to the test subject 2 by showing information indicating evoking contents instructing the test subject 2 to evoke, information indicating the result of classifying cerebral activity and other information on the screen 84.

2. Configuration of Computer

Figure 2:
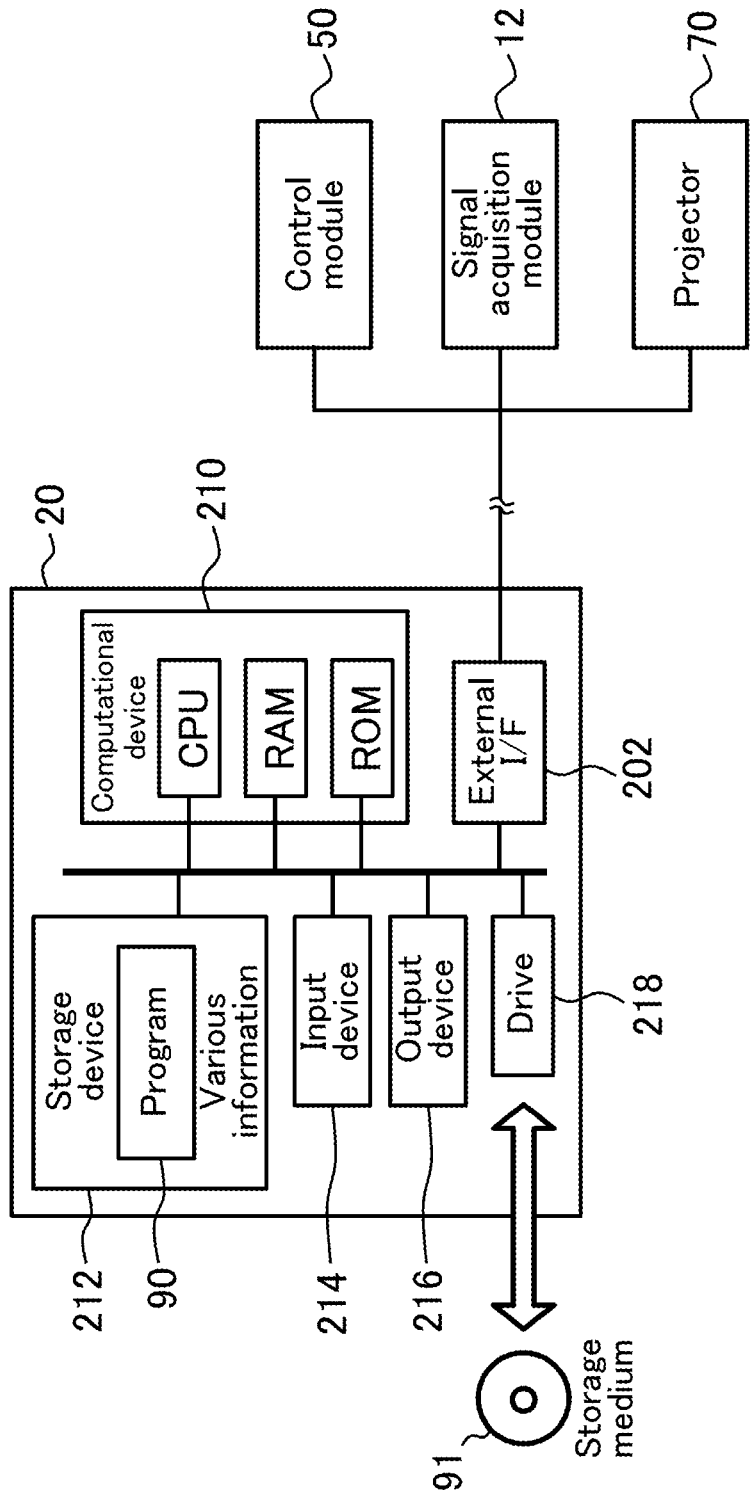
FIG. 2 schematically illustrates a hardware configuration of a computer according to the embodiment.

Next, an example of the hardware configuration of the computer 20 according to the present embodiment will be described, using FIG. 2. FIG. 2 schematically illustrates an example of the hardware configuration of the computer 20 according to the present embodiment.

As shown in FIG. 2, the computer 20 according to the present embodiment is an information processing device to which a computational device 210, a storage device 212, an external interface 202, an input device 214, an output device 216 and a drive 218 are electrically connected. As a result of these devices, the computer 20 is configured to receive cerebral activity signals from the signal acquisition module 12, send commands to the control module 50, and control the display contents of the projector 70. Note that, in FIG. 2, the external interface is denoted as "External I/F".

The computational device 210 includes a CPU (Central Processing Unit) which is hardware processor, a RAM (Random Access Memory) and a ROM (Read Only Memory), and controls the constituent elements according to information processing. The storage device 212 is an auxiliary storage device such as a hard disk drive or a solid-state drive, for example, and stores a computer program 90 that is executed by the computational device 210 and various types of information such as cerebral activity signal data, display contents of the projector 70 and transition patterns of cerebral activity discussed below.

The program 90 is a computer program for causing the computer 20 to execute information processing for teaching the motion of a predetermined motor pattern to the test subject 2, while analyzing the class of cerebral activity of the test subject 2. A detailed description will be given later.

The external interface 202 is appropriately selected according to the external device that is to be connected. In the present embodiment, the computer 20 is connected to the signal acquisition module 12 (brainwave sensor 10), the control module 50 (force presentation device 80), and the projector 70, via this external interface 202.

The input device 214 is a device for performing input such as a mouse or a keyboard, for example. Also, the output device 216 is a device for performing output such as a display or a speaker, for example. An operator is able to operate the computer 20, via the input device 214 and the output device 216.

The drive 218 is a drive device such as a CD drive or a DVD drive, and is for loading programs stored in a storage medium 91, for example. The type of drive 218 may be appropriately selected according to the type of storage medium 91. The program 90 and various types of information may be stored in this storage medium 91.

The storage medium 91 is a medium that accumulates, through an electric, magnetic, optical, mechanical or chemical action, information such as programs and the like recorded on a computer or a device or machine, so as to enable reading of information such as the programs and the like. The storage medium 91 is a medium that accumulates, through an electric, magnetic, optical, mechanical or chemical action, information such as recorded programs, in a manner that enables a computer or other device or machine to read information such as the programs. The computer 20 may acquire the program 90 and various types of information from this storage medium 91.

FIG. 2 illustrates a disk-type storage medium such as a CD or DVD, as an example of the storage medium 91. However, the type of storage medium 91 is not limited to a disk-type storage medium, and may be other than a disk-type storage medium. A semiconductor memory such as a flash memory, for example, can be given as a storage medium other than a disk-type storage medium.

Note that, in relation to the specific hardware configuration of the computer 20, constituent elements can be omitted, replaced or added as appropriate, according to the embodiment. For example, the computer 20 may be provided with a plurality of computational devices 210. The computational device 210 may also include a plurality of processors. Also, in FIG. 2, the computer 20 is represented as one computer. However, the computer 20 need not be limited to such an example, and may be constituted by a plurality of computers. In this case, each computer may be provided with a plurality of computational devices. Also, the computer 20 may be a general-purpose PC (Personal Computer), a server device or the like, apart from an information processing device designed exclusively for services that are provided. Furthermore, the program 90 and various types of information may be stored in storage device such as a NAS (Network Attached Storage) on a network, and the computer 20 may acquire the program 90 and various types of information via the network. Also, the computer 20 may be connected to the signal acquisition module (brainwave sensor 10), the control module 50 (force presentation device 80) and the projector 70 via a network.

3. Motor Teaching

Figure 3:
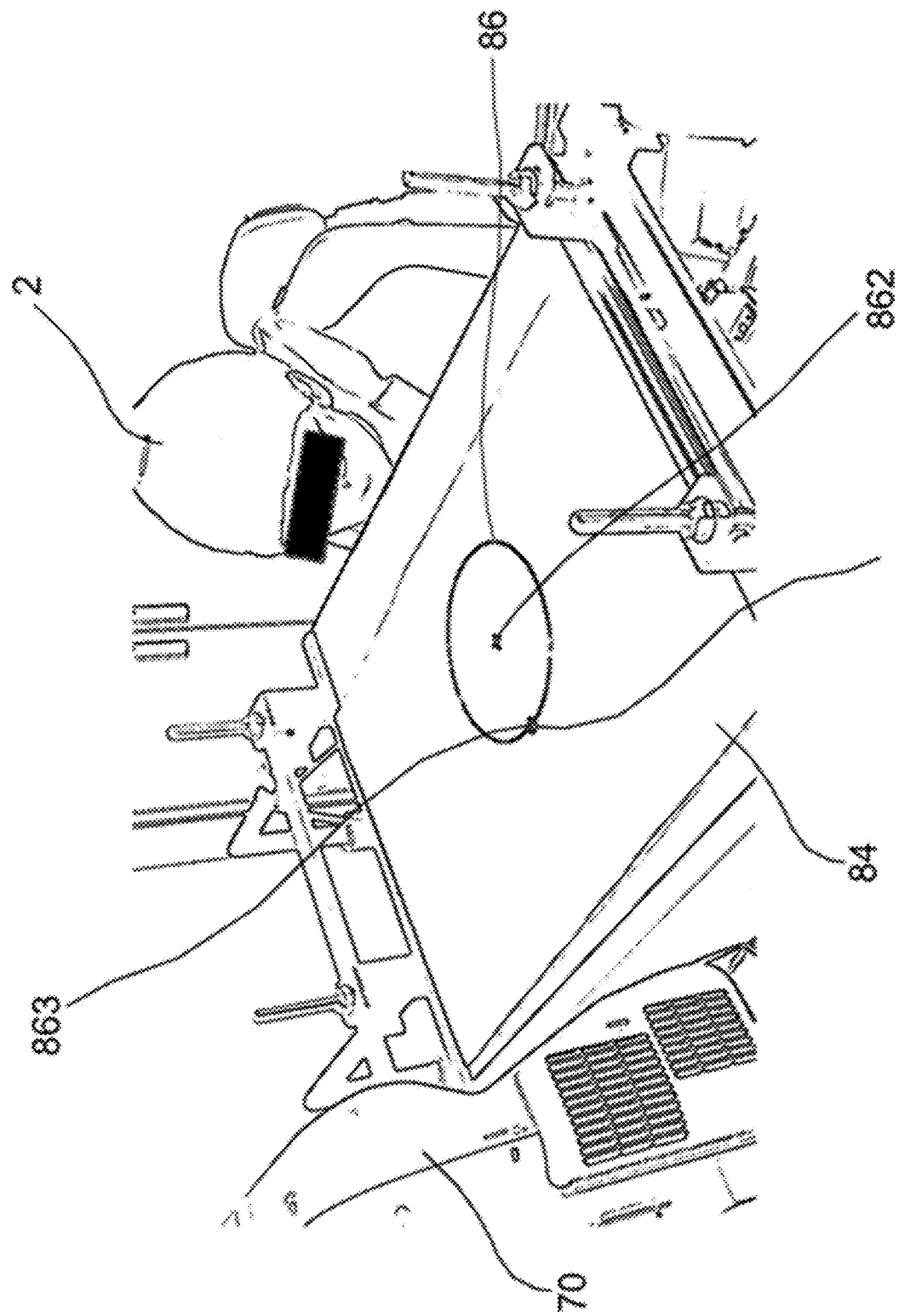
FIG. 3 is a diagram for describing a state of passive motor training on a subject using a force presentation device (operation device).

Next, a method of teaching motion to the test subject 2 will be described, using FIG. 3. FIG. 3 illustrates a situation in which passive motor teaching is performed on the test subject 2 by the force presentation device 80.

The example of FIG. 3 shows a state of motor learning of the upper limbs. Although the test subject 2 is holding the operation part 82 with his or her hand on the lower side of the screen 84, and, as shown in FIG. 3, the test subject 2 is preventing from directly seeing the position of the operation part 82 (i.e., the position of his or her hand) by the screen 84.

Prior to motor teaching, a trajectory 86 of the motor pattern that is to be learned and a start position 861 (circle) and a point of regard 862 (+sign) of the trajectory 86 are projected onto the screen 84 by the projector 70. Also, a point 863 indicating the position of the operation part 82 (i.e., position of his or her hand) is also projected, and the test subject 2 is thereby able to guide the position of his or her hand to the starting position 861.

During motor teaching, the trajectory 86 and the starting position 861 are not shown, and the operation part 82 of the force presentation device 80 is driven to draw the trajectory 86 of the motor pattern. The test subject 2 thereby learns motion of his or her hand passively, relying only on a sense of force and not vision.

Here, the following findings were obtained as a result of tests that will be described later.

(1) The degree to which motion is mastered significantly improves when the cerebral activity of the test subject 2 is in a motor imagery state (motor imagery class), during the period of passive motor teaching of the test subject 2 by the force presentation device 80.

(2) Whether the cerebral activity of the test subject 2 will be in the motor imagery state (motor imagery class) during the period of motor teaching is individually dependent on each test subject 2, depending on which state (class) the cerebral activity of the test subject 2 was in during the preceding stage of period of motor teaching.

Figure 16:
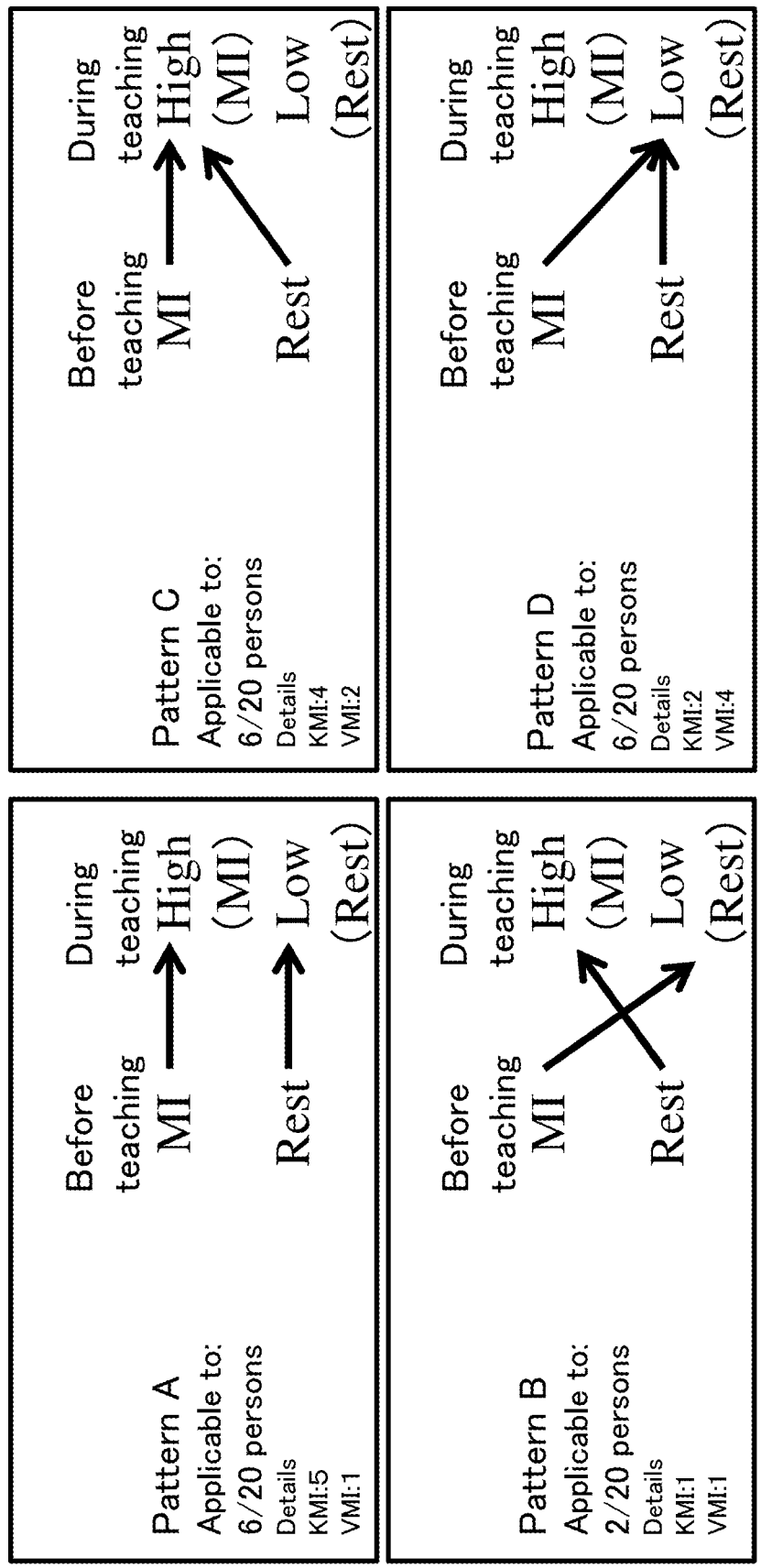
FIG. 16 shows the relationship between the state of cerebral activity prior to teaching and the state of cerebral activity during teaching.

For example, some test subjects will be in the "motor imagery state" during the period of motor teaching when their cerebral activity is in the "motor imagery state" in the preceding stage of the motor teaching period, and some test subjects will be in the "motor imagery state" during the period of motor teaching when their cerebral activity is in the "rest state" in the preceding stage of the motor teaching period. In view of this, such a relationship between the state of cerebral activity in the preceding stage of the motor teaching period and the state of cerebral activity during the motor teaching period will be referred to as the "transition pattern" of the test subject. According to the findings of empirical testing discussed below, the following four transition patterns were found to exist (see FIG. 16 discussed below).

(A) Cerebral activity during the motor teaching period will be in the "motor imagery state" when cerebral activity prior to motor teaching is in the "motor imagery state". On the other hand, cerebral activity during the motor teaching period will be in the "rest state" when cerebral activity prior to motor teaching is in the "rest state".

(B) Cerebral activity during the motor teaching period will be in the "rest state" when cerebral activity prior to motor teaching is in the "motor imagery state". On the other hand, cerebral activity during the motor teaching period will be in the "motor imagery state" when cerebral activity prior to motor teaching is in the "rest state".

(C) Cerebral activity during the motor teaching period will be in the "motor imagery state", irrespective of the class of cerebral activity prior to motor teaching.

(D) Cerebral activity during the motor teaching period will be in the "rest state", irrespective of the class of cerebral activity prior to motor teaching.

In view of this, the motor teaching system 1000 according to the present embodiment specifies the transition pattern to which the cerebral activity of the test subject 2 belongs, and determines the class into which to guide the cerebral activity of the test subject 2 in the preceding stage of motor teaching period, based on the specified transition pattern. The motor teaching system 1000 according to the present embodiment allows the test subject 2 to passively learn motion of his or her hand, after having guided the cerebral activity of the test subject 2 to be in the motor imagery state, during the period of motor teaching, thereby enabling the test subject 2 to efficiently master motor patterns.

4. Functional Configuration of Computer

Figure 4:
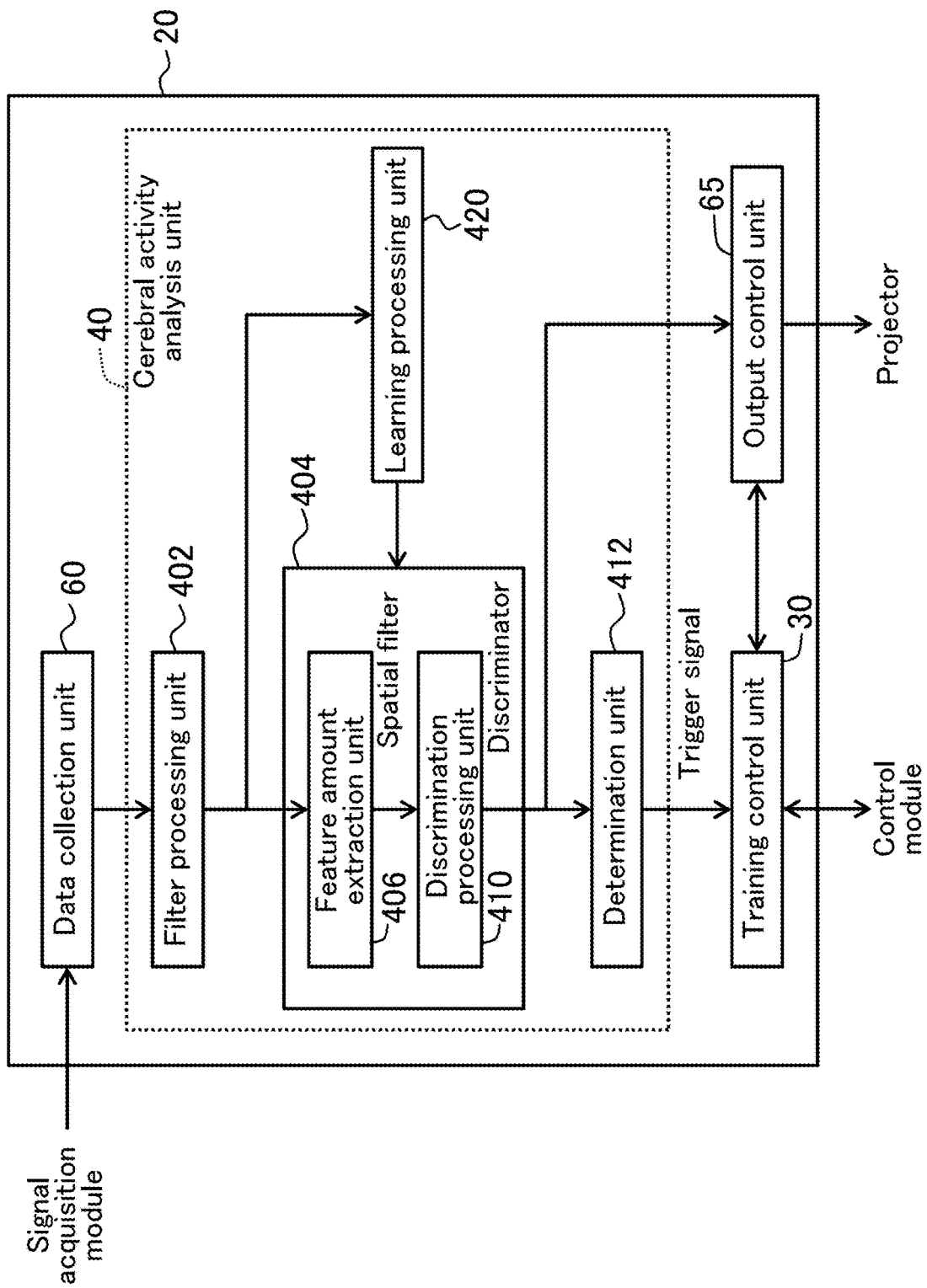
FIG. 4 schematically illustrates a functional configuration of the computer according to the embodiment.

Next, the functional configuration of the computer 20 for classifying the class of the cerebral activity of the test subject 2 will be described, using FIG. 4. FIG. 4 schematically illustrates an example of the functional configuration of the computer 20 for classifying the class of the cerebral activity of the test subject 2.

The computational device 210 of the computer 20 extracts the program 90 stored in the storage device 212 to the RAM. The computational device 210 then uses the CPU to interpret and execute the program 90 extracted to the RAM, and controls the constituent elements. As shown in FIG. 4, the computer 20 according to the present embodiment thereby functions as an information processing device comprising a data collection unit 60, a cerebral activity analysis unit 40, a training control unit 30, and an output control unit 65.

The data collection unit 60 acquires a set of a cerebral activity signal from when motor imagery is carried out by the test subject 2 and a cerebral activity signal from when imagery other than motor imagery is carried out (rest state in the present embodiment) as a training data set, prior to motor teaching. The training data set is acquired from the brainwave sensor 10 that is being worn by the test subject 2, via the signal acquisition module 12 and the external interface 202. The acquired training data set may be stored in the storage device 212 until it is utilized.

The cerebral activity analysis unit 40, by decoding the cerebral activity signal (brainwave signal) acquired from the brainwave sensor 10, classifies the cerebral activity of the test subject 2 into one of a plurality of classes including the motor imagery class. In order to execute such decoding processing, the cerebral activity analysis unit 40 according to the present embodiment comprises a filter processing unit 402, a decoder 404, a determination unit 412, and a learning processing unit 420.

In the present embodiment, in order to utilize a dry wireless headset as the brainwave sensor 10, the cerebral activity signal is acquired as a brainwave (EEG: Electroencephalogram) signals. This EEG signal is collected using a plurality of channels (e.g., F7, Fp1, Fp2, F8, F3, Fz, F4, C3, Cz, P8, P7, Pz, P4, T3, P3, O1, O2, C4, T4 according to the International 10-20 system) as well as a reference signal and ground potential.

The filter processing unit 402, by applying a bandpass filter to the acquired EEG signal, extracts a predetermined frequency component (7-30 Hz in the present embodiment). The decoder 404 is provided with a feature amount extraction unit 406 and a discrimination processing unit 410, in order to decode the predetermined frequency component extracted from the EEG signal. The feature amount extraction unit 406 extracts the feature amount from the predetermined frequency component of the EEG signal, utilizing a spatial filter. The discrimination processing unit 410, by inputting the feature amount to a discriminator, acquires an output value that can identify the class of cerebral activity from the discriminator. The determination unit 412, by comparing this output value with a predetermined threshold, distinguishes the class of the current cerebral activity.

The learning processing unit 420 generates the spatial filter and the discriminator that are utilized by the decoder 404 by machine learning, utilizing the training data set collected by the data collection unit 60. In the present embodiment, a CSP algorithm and a feature selection algorithm discussed below are utilized in generating the spatial filter and the discriminator. The decoder 404 is thereby configured to be capable of outputting an output value that can determine the class into which the cerebral activity of the test subject 2 is to be classified, out of the two classes of the motor imagery class and the rest class. A detailed description will be given later.

The training control unit 30 outputs commands for controlling the operations for teaching a motor pattern by the force presentation device 80. As described above, in the present embodiment, the cerebral activity of the test subject 2 is guided so as to be classified into one of the motor imagery class and the rest class, prior to motor teaching. Thus, in the case where it is determined, as a result of performing threshold determination of the output value of the decoder 404, that the cerebral activity of the test subject 2 has been classified into the target class, the determination unit 412 outputs a trigger signal for starting motor teaching to the training control unit 30. The training control unit 30 instructs the force presentation device 80 to start operations for teaching a motor pattern, using this trigger signal.

5. Method of Creating Decoder

Next, a method of creating a decoder capable of classifying the state of cerebral activity, or specifically, the spatial filter and the discriminator that are utilized by the decoder 404, will be described. For example, the following Known Literature 2 and Known Literature 3 disclose technologies that combine an adaptive spatial filter and a classifier that uses adaptive linear discriminant analysis (LDA).

Known Literature 2: W. Wojcikiewicz, C. Vidaurre, and M. Kawanabe, "Improving classification performance of bcis by using stationary common spatial patterns and unsupervised bias adaptation", in Hybrid Artificial Intelligent Systems, ser. Lecture Notes in Computer Science. Springer Berlin Heidelberg, 2011, vol. 6679, pp. 34-41.

Known Literature 3: R. Tomioka, J. Hill, B. Blankertz, and K. Aihara, and "Adapting spatial filtering methods for nonstationary bcis" transformation, vol. 10, p. 1, 2006.

Also, in the present embodiment, the cerebral activity analysis unit 40 classifies the cerebral activity of the test subject 2 into one of the motor imagery class and the rest class. That is, there are two classes into which cerebral activity is classified. A conventional robust CSP (Common Spatial Patterns) algorithm can be utilized, in order to find a spatial filter with which the difference in variance between these two classes is at a maximum. This conventional robust CSP algorithm is disclosed in the following Known Literature 4, for example.

Known Literature 4: X. Yong, R. K. Ward, and G. E. Birch, "Robust common spatial patterns for eeg signal preprocessing". Conference proceedings: Annual International Conference of the IEEE Engineering in Medicine and Biology Society. IEEE Engineering in Medicine and Biology Society. Annual Conference, vol. 2008, pp. 2087-2090, 2008.

Hereinafter, the robust CSP algorithm will be briefly described on the basis of the contents of Known Literature 4. Note that, as will be discussed later, with the CSP algorithm, a plurality of filters that perform adaptive weighting processing on a covariance matrix of EEG signals that are acquired from electrodes disposed at multiple places on the user's scalp and extract feature amounts are created. These filters that perform weighting processing are the above "spatial filters".

CSP Algorithm

The CSP algorithm is frequently used as a technique for extracting feature amounts, in the classification problem of two classes ($C_1$ or $C_2$) of BMI that is based on rhythmic modulation by motor imagery. For example, the motor imagery state is class $C_1$, and the rest state is class $C_2$.

Here, a set S of the signals of the trials is defined with the following Equation 1, where N is number of samples that are included in every one trial, and M is the number of a training sets.

$$S=\{S_1, S_2, \ldots, S_M\}, S_i \in R^{p \times N} \qquad \text{Equation 1}$$

Also, the optimization problem of the CSP algorithm is represented with the following Equation 2.

$$\max_\omega \sum_{i \in C_1} \text{var}(\omega^T S_i) \qquad \text{Equation 2}$$
$$\text{subject to} \sum_{i=1}^{M} \text{var}(\omega^T S_i) = 1$$
$$\omega \in R^p$$

Note that $C_1$ represents all of the EEG trials of class $C_1$, and ω is an unknown weight vector or weight matrix of the spatial filter. A var function can be calculated as shown in the following Equation 3.

$$\text{var}(\omega^T S_i) = \omega^T E[\{S_i - E(S_i)\}\{S_i - E(S_i)\}^T]\omega \qquad \text{Equation 3}$$
$$= \omega^T \Lambda_i \omega$$

Here, $\Lambda_1$ and $\Lambda_2$ are respectively covariance matrices of the EEG signals belonging to class $C_1$ and class $C_2$.

The CSP algorithm can be summarized in the following processing (I) to (III).

(I) Execute whitening transformation on matrix $\Lambda=(\Lambda_1+\Lambda_2)$. That is, whiten matrix $\Lambda$, by finding matrix P (whitening matrix) that satisfies a condition such as shown in the following Equation 4, through eigenvalue decomposition on matrix $\Lambda=(\Lambda_1+\Lambda_2)$. Note that, in Equation 4, the relationship shown in the following Equation 5 holds.

$$P(\Lambda_1+\Lambda_2)P^T=I \qquad \text{Equation 4}$$

$$\Lambda=\Lambda_1+\Lambda_2=\Phi U \Phi^T \qquad \text{Equation 5}$$

holds through eigenvalue decomposition on $\Lambda$.

$$\hat{\Lambda}_1 + \hat{\Lambda}_2 = P(\Lambda_1 + \Lambda_2)P^T$$
$$= U^{-1/2}\Phi^T \Lambda (U^{-1/2}\Phi^T)^T$$
$$= U^{-1/2}\Phi^T \Phi U \Phi^T \Phi U^{-1/2}$$
$$= U^{-1/2}(\Phi^T \Phi) U (\Phi^T \Phi) U^{-1/2}$$
$$= I$$

where $P=U^{-1/2}\Phi^T$ is the whitening matrix, and assuming $\hat{\Lambda}_1=P\Lambda_1 P^T$ and $\hat{\Lambda}_2=P\Lambda_2 P^T$.

U is an eigenvalue diagonal matrix with eigenvalues in the diagonal component

φ is an eigenvector matrix formed by aligning eigenvectors (II) Calculate an orthogonal matrix R and a diagonal matrix D, by performing eigenvalue decomposition so as to satisfy the condition that is shown by the following Equation 6.

Perform eigenvalue decomposition such that $$\hat{\Lambda}_1=RDR^T, \hat{\Lambda}_2=R(I-D)R^T. \qquad \text{Equation 6}$$

That is, $\hat{\Lambda}_1$ and $\hat{\Lambda}_2$ can undergo eigenvalue decomposition with a common eigenvector matrix.

At this time, $$R^T \hat{\Lambda}_1 R = R^T (P\Lambda_1 P^T)R$$
$$= R^T P \Lambda_1 P^T R$$
$$= D$$

(III) Calculate a projection matrix $W=R^T P$ for class $C_1$ and class $C_2$, and take a row vector ω of the calculated projection matrix W as a CSP filter, as shown in the following Equation 7. This CSP filter is the above spatial filter. Note that since the projection matrix W includes a plurality of row vectors ω, a plurality of CSP filters are generated at this stage.

Equation 7

When $W=R^T P$, ω is, for example, the row of W corresponding to m eigenvalues with respect to larger $D$ On the other hand, with regard to $C_2$, the row of W corresponding to m eigenvalues, for example, can be given as co with respect to smaller $D$.

The squared mean value (or the log scale value) of $z_p(t)$ which is the projected result of multiplying the covariance matrix by each of the generated CSP filters can be used as the feature amount. Hereinafter, it is assumed that the log scale value is used as the feature amount. For example, the value shown in the following Equation 8 can be used as this feature amount.

$$f_P = \log(E[z_p^2])  \quad\quad\quad \text{Equation 8}$$

Note that, apart from the above, it is also possible to use, as the feature amount, the variance of $z_p(t)$ which is the above projected result, a value obtained by standardizing the variance of $z_p(t)$, or the log scale value of either of these values. A discriminator can then be generated by performing linear discriminant analysis (LDA) on such a feature amount, and it becomes possible to execute class classification of EEG signals, by utilizing the CSP filters and the discriminator.

Feature Selection Algorithm

Next, an example of a feature selection algorithm for selecting an optimal CSP filter, that is, the CSP filter with the highest cerebral activity discrimination performance among the plurality of CSP filters will be described.

First, a decision tree for each feature amount that is obtained by projecting the covariance matrix of the EEG signals with each CSP filter is created using a random forest method. Next, the importance of each feature amount is derived, based on the created decision trees, and the mean importance value for each feature amount is taken as the contribution of each CSP filter. The CSP filter with the highest contribution is selected for use, by comparing the respective contributions of the CSP filters. The optimal CSP filter can thereby be selected from among the plurality of CSP filters. Note that the following Known Literature 5 may be referenced with regard to the feature selection algorithm.

Known Literature 5: P. Geurts, D. Ernst, and L. Wehenkel, "Extremely randomized trees", Machine Learning, 63(1), 3-42-2006.

Note that the method of selecting the optimal CSP filter from among the plurality of CSP filters need not be limited to such a method, and can be selected as appropriate according to the embodiment. For example, a discriminator may be generated by linear discriminant analysis discussed below for each CSP filter. The discrimination performance on each EEG signal of the training data set may then be calculated using each CSP filter and each discriminator, and the CSP filter with the highest calculated discrimination performance may be selected for use.

Generation of Decoder

Next, the process in which the computer 20 (learning processing unit 420) creates the CSP filters and discriminators of the decoder utilizing the CSP algorithm and the feature selection algorithm will be described.

First, the data collection unit 60 collects EEG signals of the test subject 2. The data collection unit 60 thereby acquires a set of an EEG signal from when motor imagery is carried out and an EEG signal from when imagery other than motor imagery is carried out (rest state in the present embodiment) as a training data set. The filter processing unit 402 applies bandpass filtering (7-30 Hz) to each EEG signal of the acquired training data set, and extracts a predetermined frequency component.

Next, the learning processing unit 420 calculates a corresponding projection matrix W, by applying the CSP algorithm to the predetermined frequency component of each EEG signal of the training data set, and thereby obtains a plurality of CSP filters. The learning processing unit 420 then selects the CSP filter with the highest contribution, or in other words, the CSP filter with the highest discrimination performance on the cerebral activity of the test subject, from the plurality of CSP filters, by applying the feature selection algorithm on the plurality of CSP filters.

Here, in the case where the selected CSP filter appears to the operator who operates the computer 20 to clearly be an error, the operator may operate the computer 20 to correct the selected CSP filter or replace the selected CSP filter with another CSP filter. At this time, the operator may operate the computer 20 to select an CSP filter to be appropriately utilized from among the plurality of CSP filters generated by the CSP algorithm.

The learning processing unit 420 then creates a discriminator, by performing linear discriminant analysis on the feature amount that is obtained by projecting the covariance matrix of each EEG signal of the training data set with the selected CSP filter. For example, the learning processing unit 420 is able to create a (linear) discriminator, by utilizing logistic regression as a model of linear discrimination. The decoder is thereby completed. That is, the creation of CSP filters and discriminators to be utilized by the decoder 404 is completed. On the other hand, in the case where a discriminator is created in the selection process of a CSP filter, this processing can be omitted, and the decoder is completed at the point in time at which selection of a CSP filter is completed.

Note that a logistic function generates a continuous probability output between 0 and 1. Thus, for example, it can be indicated that the cerebral activity is to be classified into the rest state class as the output of the discriminator approaches 0, and that the cerebral activity is to be classified into the motor imagery class as the output of the discriminator approaches 1. Thus, the determination unit 412 is able to determine whether the current cerebral activity of the test subject 2 is the "motor imagery" class or the "rest state" class, by comparing the output of the discriminator with a predetermined threshold.

In the above description, a method of generating a decoder utilizing the CSP algorithm, the feature selection algorithm and the linear discrimination method was described. However, the method of generating a decoder that decodes the cerebral activity of test subjects need not be limited to such an example. A method of detecting event-related desynchronization (ERD) through independent component analysis (ICA), Laplacian filtering or the like, for example, may be employed as the method of extracting feature amounts. Spatial filters of a type other than CSP filters may thereby be used in extracting the feature amount of EEG signals. Also, a method that combined a plurality of algorithms such as combining ICA with the CSP algorithm, for example, may be employed as the method of extracting feature amounts. Also, a method of utilizing a support vector machine or the like may be employed as the discrimination method. Furthermore, the computer 20 (cerebral activity analysis unit 40) according to the present embodiment classifies the cerebral activity of the test subject 2 into the two classes of "motor imagery" and "rest state". However, the number of the classes for classification may be three or more, as long as the "motor imagery" class is included.

6. Flow of Motor Teaching

Figure 5:
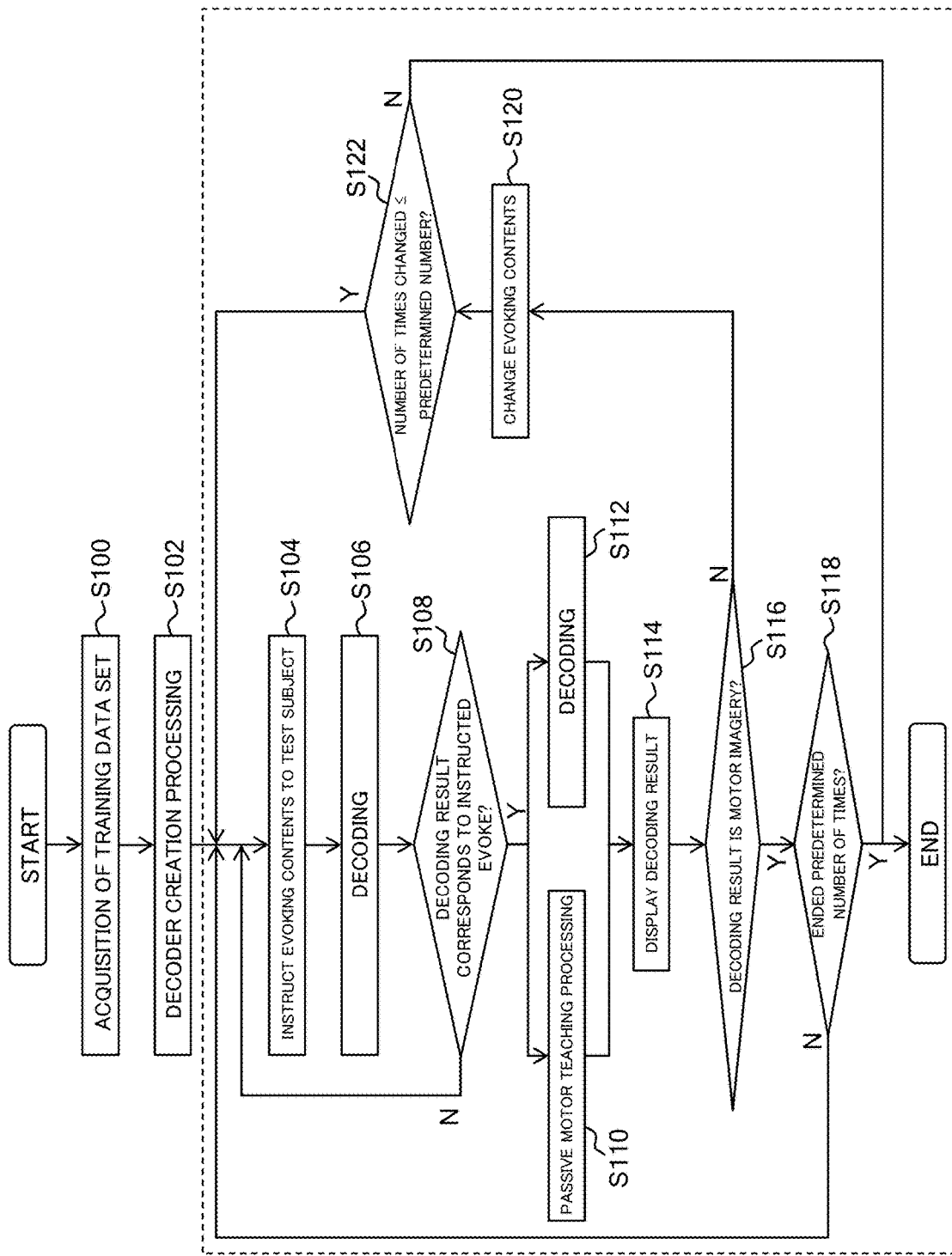
FIG. 5 shows an example of a processing procedure of the motor teaching system according to the embodiment.

Next, a procedure for teaching motion to the test subject 2 will be described, using FIG. 5. FIG. 5 is a flowchart showing a procedure for teaching motion to the test subject 2 using the motor teaching system 1000 according to the present embodiment.

Step S100

First, in step S100, the computational device 210 of the computer 20 functions as the data collection unit 60, and acquires a training data set, prior to teaching of a motor pattern by the force presentation device 80.

For example, the test subject 2 is instructed to carry out motor imagery and the rest state alternately for several seconds. The computational device 210 acquires an EEG signal at this time from the brainwave sensor 10, via the external interface 202 and the signal acquisition module 12. The computational device 210 then extracts a portion from when motor imagery is carried out and a portion from when the rest state is carried out from the acquired EEG signal. The computational device 210 thereby acquires, with regard to the test subject 2, a set of an EEG signal from when motor imagery is carried out and an EEG signal from when imagery other than motor imagery is carried out (rest state) as a training data set.

Step S102

In the following step S102, the computational device 210 functions as the learning processing unit 420, and creates a spatial filter and a discriminator that are to be utilized in decoding the cerebral activity of the test subject 2, based on the training data set. In the present embodiment, the computational device 210 generates an optimal CSP filter and discriminator for detection of motor imagery by machine learning that utilizes the CSP algorithm and the feature selection algorithm. The computational device 210 then sets the generated CSP filter and discriminator in the decoder 404 of the cerebral activity analysis unit 40. Preparation for motor teaching is thereby completed, and it becomes possible to analyze the cerebral activity of the test subject 2, or specifically, to classify the cerebral activity of the test subject 2 into the motor imagery class or the rest state class.

Step S104

In the following step S104, the computational device 210 outputs evoking contents to be performed to the test subject 2 prior to teaching of a motor pattern discussed below (step S110), such that the cerebral activity of the test subject 2 during the period of teaching of the motor pattern is classified into the motor imagery class. In the present embodiment, the computational device 210 functions as the training control unit 30, and uses the projector 70 to project the evoking contents (may be referred to as "prerequisite evoking contents") to be evoked by the test subject 2 on the screen 84. The computational device 210 thereby instructs to the test subject 2 to evoke the evoking contents, prior to teaching of the motor pattern.

As described above, there are a plurality of transition patterns of cerebral activity from prior to teaching to during teaching. The computer 20 stores information on these transition patterns in the storage device 212. In the initial stage prior to motor teaching in which the transition pattern of the test subject 2 is has not been specified, the transition pattern of the cerebral activity of the test subject 2 is unknown. Thus, in this case, the computational device 210 may output either of a "motor imagery" instruction or a "rest state" instruction, as a evoking contents instruction. Hereinafter, for convenience of description, the computational device 210 is assumed to output "rest state" as the evoking contents, in the initial stage in which the transition pattern of the test subject 2 is unknown.

Step S106

In the following step S106, the computational device 210 acquires the EEG signal of the test subject 2 from the brainwave sensor 10, while instructing the test subject 2 to evoke the evoking contents. Next, the computational device 210 functions as the filter processing unit 402, and applies a bandpass filter to the acquired EEG signal to extract a predetermined frequency component (7-30 Hz). The computational device 210 then functions as the decoder 404, and applied the CSP filter and discriminator set in above step S102 to the extracted frequency component. The computational device 210 thereby decodes EEG signal of the test subject 2 that is acquired prior to teaching of the motor pattern.

In the present embodiment, the computational device 210 controls the projector 70 to display this decoding result on the screen 84 as feedback information. That is, the computational device 210 feeds back the result of having classified the cerebral activity of the test subject 2, prior to teaching of the motor pattern. The test subject 2 is thereby able to recognize the result discriminated by the decoder 404 while he or she is currently evoking the evoking contents. As a result, the test subject 2 will make an effort for a predetermined time such that decoding result of evoking the instructed evoking contents is achieved, based on the feedback information.

Figure 12:
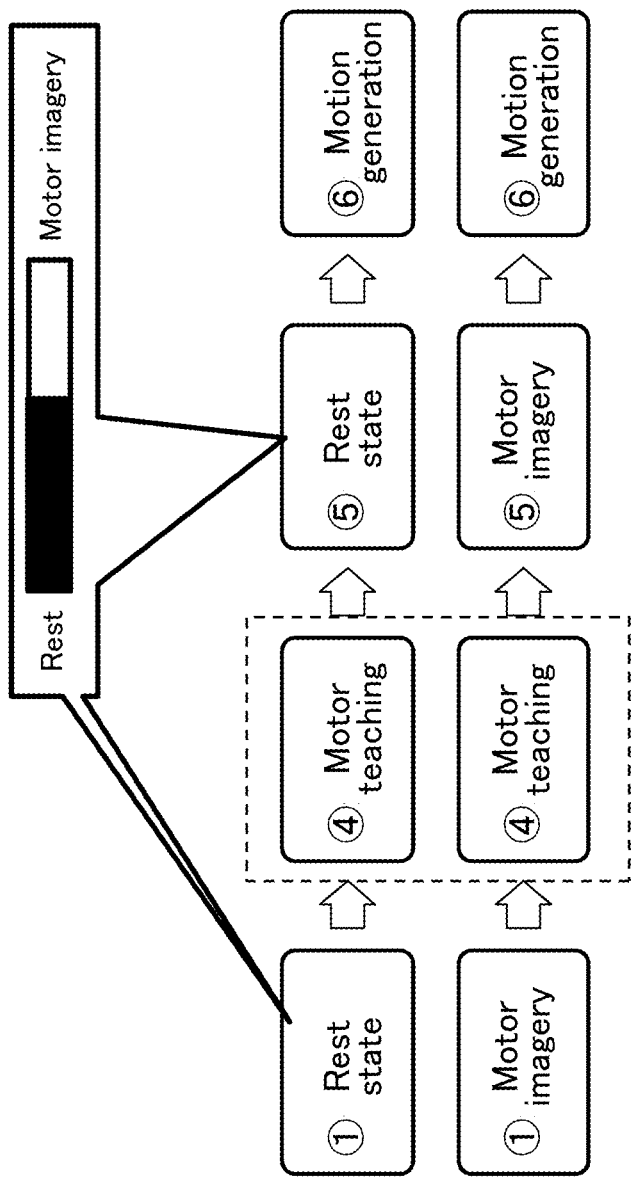
FIG. 12 is a conceptual diagram for describing evoking contents for instructing a test subject before and after motor teaching.

Here, the method of presenting the feedback information may be appropriately determined according to the embodiment. For example, the computational device 210, as shown in FIG. 12 discussed below, may also employ a presentation method such as displaying a bar on the screen 84, and indicating that motor imagery is being carried out when the bar deforms to approach one end and indicating the rest state when the bar deforms to approach the other end. In this case, the computational device 210 is able to determine the length of the bar based on the output value of the discriminator of the decoder 404.

Note that graphics displayed on the screen 84 are not limited to a bar as long as the shape thereof enables the test subject to be presented with whether cerebral activity approaching the designated evoking contents is being carried out. A circular sector that is drawn within a circle, for example, can be given as one such other shape. Also, rather than a level such as the length of a bar or size of a circular sector, the computational device 210 may display the result of functioning as the determination unit 412, that is, the class of the cerebral activity of the test subject 2 classified by comparing the output value of the discriminator with a threshold on the screen 84.

In the following step S108, the computational device 210 functions as the training control unit 30, and determined whether the cerebral activity of the test subject 2 is classified into the class corresponding to the evoking contents instructed in step S104, based on the decoding result of the above step S106. That is, the computational device 210 functions as the determination unit 412, and determines whether the classified class of the cerebral activity of the test subject 2 is the class corresponding to the evoking contents, as a result of comparing the output value of the discriminator with the threshold. If the cerebral activity of the test subject 2 is classified into the class corresponding to the evoking contents (Y in S108), the computational device 210 outputs a trigger signal, and advance the processing to the following steps S110 and S112. On the other hand, if the cerebral activity of the test subject 2 is not classified into the class corresponding to the evoking contents (N in S108), the processing is returned to step S104.

Steps S110 and S112

In response to the cerebral activity of the test subject 2 being classified into the class corresponding to the evoking contents (in response to output of the trigger signal), the computational device 210, in the following step S110, functions as the training control unit 30, and outputs a command instructing the force presentation device 80 (control module 50) to start operations for teaching the motor pattern. Passive teaching of the motor pattern (proprioceptive training) is thereby implemented on the test subject 2.

Also, together with executing step S110, the computational device 210 functions as the cerebral activity analysis unit 40, and executes the processing of step S112 to analyze the state of the cerebral activity of the test subject 2 during the motor teaching. That is, the computational device 210 acquires the EEG signal of the test subject 2 from the brainwave sensor 10 during the period in which the force presentation device 80 is being caused to execute the operations for teaching the motor pattern. The computational device 210 then decodes the EEG signal by a similar process to step S106.

During the period of teaching the motor pattern, however, the computational device 210 does not feed back the result of having classified the cerebral activity of the test subject 2, unlike in the above step S106. That is, the result discriminated by the decoder 404 is not displayed on the screen 84 as feedback information while the test subject 2 is currently evoking the evoking contents. When feedback information is displayed during teaching of the motor pattern, the test subject 2 will simultaneously be required to carry out both the task of motor training and the task of hoping that the decoding result corresponds to the instructed evoking contents (evoking the evoking contents). Thus, it will be necessary to execute dual tasks, and the difficulty of the tasks will be increased unnecessarily. In order to avoid this, in the present embodiment, the computational device 210 does not display feedback information to the test subject 2. Note that the computational device 210 according to the present embodiment may display feedback information to a third party (e.g., trainer) other than the test subject 2.

Step S114

In the following step S114, the computational device 210 controls the projector 70, after teaching of the motor pattern has ended, to display the result of having decoded the EEG signal acquired from the brainwave sensor 10 during the period of teaching the motor pattern as a result of step S112 on the screen 84. The computational device 210 thereby displays on the screen 84 whether the cerebral activity of the test subject 2 during the period of teaching the motor pattern is classified into the motor imagery class, or in other words, whether the class into which the cerebral activity of the test subject 2 was classified is the motor imagery class.

Thus, in the present embodiment, the evoking contents instructed prior to teaching of the motor pattern and the classified class of cerebral activity during the period of teaching the motor pattern are displayed on the screen 84 as a result of steps S106 and S114. Trainers such as sports coaches and rehabilitation therapist are thereby able to know the transition pattern of the test subject 2, as a result of which a learning program that determines the procedure for motor teaching can be appropriately determined for every test subject 2.

Steps S116 to S122

In the following step S116, the computational device 210 functions as the training control unit 30, and determines whether the cerebral activity of the test subject 2 during the period of teaching the motor pattern was classified into the motor imagery class, as a result of decoding the EEG signal of the test subject 2 acquired from the brainwave sensor 10 during the period of teaching the motor pattern. If the cerebral activity of the test subject 2 is classified into a class other than motor imagery (i.e., rest state class) (N in step S116), the computational device 210 advances processing to the following step S120. On the other hand, if the cerebral activity of the test subject 2 was classified into the motor imagery class, the computational device 210 advances processing to the following step S118.

In the following step S118, the computational device 210 functions as the training control unit 30, and determines whether teaching of the motor pattern has ended a predetermined number of times. If teaching of the motor pattern has not ended a predetermined number of times (N in S118), the computational device 210 returns the processing to step S104. On the other hand, if teaching of the motor pattern has ended a predetermined number of times (Y in S118), the computational device 210 ends motor teaching by the motor teaching system according to the present embodiment.

In the following step S120, the computational device 210 changes the evoking contents instructed in step S104. For example, if the "rest state" is instructed prior to motor teaching, and the cerebral activity during motor teaching is also in the "rest state", the transition pattern of the test subject 2 is assumed to be the pattern of (A) or (D) above. Thus, in this case, the computational device 210 determines that the transition pattern of the test subject 2 is the pattern of (A) or (D) above, with reference to the information on the transition patterns stored in the storage device 212, and changes the evoking contents instructed in step S104 from "rest state" to "motor imagery".

Also, if "motor imagery" is instructed prior to motor teaching, and the cerebral activity during motor teaching is in the "rest state", it is assumed that the transition pattern of the test subject 2 is the pattern of (B) or (D) above. Thus, in this case, the computational device 210 determines that the transition pattern of the test subject 2 is the pattern of (B) or (D) above, with reference to the information on the transition patterns stored in the storage device 212, and changes the evoking contents that is instructed in step S104 from "motor imagery" to "rest state".

After changing the evoking contents that is instructed, the computational device 210, in the following step S122, determines whether the number of times that the evoking contents has been changed is less than or equal to a predetermined number of times. If the number of times that the evoking contents has been changed is less than or equal to the predetermined number of times (Y in S122), the computational device 210 returns the processing to step S104. On the other hand, if the number of times that the evoking contents has been changed exceeds the predetermined number of times (N in S122), the computational device 210 ends motor teaching by the motor teaching system according to the present embodiment.

In the present embodiment, the transition pattern of the test subject 2 can be specified, by reaching step S120 in the process of repeating that series of processing from steps S104 to S122. For example, if it is determined that the transition pattern of the test subject 2 is the pattern of (A) or (D) above, and the processing further reaches step S120 after changing the evoking contents that is instructed in step S104 from "rest state" to "motor imagery", the computational device 210 is able to specify that the transition pattern of the test subject 2 is the pattern of (D) above. On the other hand, if the processing does not reach step S120, the computational device 210 is able to specify that the transition pattern of the test subject 2 is (A) above.

Note that the processing procedure described above is merely an example of the flow of motor teaching, and the respective processing may be changed to the maximum extent possible. Also, with regard to the above processing procedure, steps can be omitted, replaced or added as appropriate, according to the embodiment.

For example, the test subject 2 may be allowed to reproduce the taught motion (also called "motion generation") himself or herself, by allowing the test subject 2 to operate the operation part 82 after step S118. The computational device 210 may then acquire position information of the operation part 82 at this time from the control module 50, and calculate a reproducibility indicating the extent to which the taught motor pattern is reproduced by the motion generation. Furthermore, the computational device 210 may present the calculated reproducibility to the test subject 2. Note that the method of calculating the reproducibility may be selected as appropriate according to the embodiment, and a calculation method according to Equation 9 discussed below may be adopted, for example.

Also, the contents of the feedback information that is displayed in the following step S106 may be reversed, after changing the evoking contents, as a result of step S120. For example, in the case of displaying the above bar as feedback information, it is indicated that motor imagery is being carried out when the end of the bar approaches one end and the rest state is indicated when the end of the bar approaches the other end. In this case, in response to having changed the evoking contents in step S120, the computational device 210 may change the settings of the feedback information so as to indicate the rest state when the end of the bar approaches one end and to indicate that motor imagery is being carried out when the end of the bar approaches the other end. The contents that are instructed in step S106 can thereby be set to always be uniform so as to lengthens display of the bar or increase the size of the circular sector. A configuration can thereby be adopted in which the test subject is easily able to intuitively recognize that the result of classifying the current cerebral activity pattern is approaching the decoding result corresponding to the specified evoking contents.

Also, in FIG. 5, the timing for starting passive teaching of the motor pattern on the test subject 2 by the force presentation device 80 is described as depending on control by the computational device 210 (training control unit 30). However, control of the timing for starting teaching of the motor pattern need not be limited to such an example, and teaching of the motor pattern may be started in response to input of an instruction from the operator of the computer 20.

As described above, with the motor teaching system 1000 according to the present embodiment, the test subject can be made to learn a motor pattern, after having provided guidance such that the cerebral activity of the test subject is in the motor imagery state, during the period of motor teaching. That is, a high learning effect can be expected, since training can be implemented after changing the cerebral activity of the test subject into a state suitable for the motor task of learning in advance. Also, according to the present embodiment, the test subject is able to efficiently learn a motor pattern, simply by passively accepting the motion provided by the operation device (force presentation device 80), without actively moving his or her body. Furthermore, according to the present embodiment, the test subject is able to know the transition pattern of cerebral activity for efficiently learning a motor pattern, simply by accepting such passive motion.

Note that by implementing the series of processing from the above steps S100 to S122, after the transition pattern of the test subject 2 is specified, the test subject 2 may remove the brainwave sensor 10, and receive an instruction to evoke the evoking contents prior to motor teaching and receive motor teaching. Also, the motor teaching system 1000 of the present embodiment can be used not only in teaching motion to a patient such as someone who is undergoing rehabilitation but more generally in teaching motion to healthy individuals. In view of this, patients and healthy individuals are referred to collectively as "learners".

7. Clustering of Spatial Filters

Figure 6:
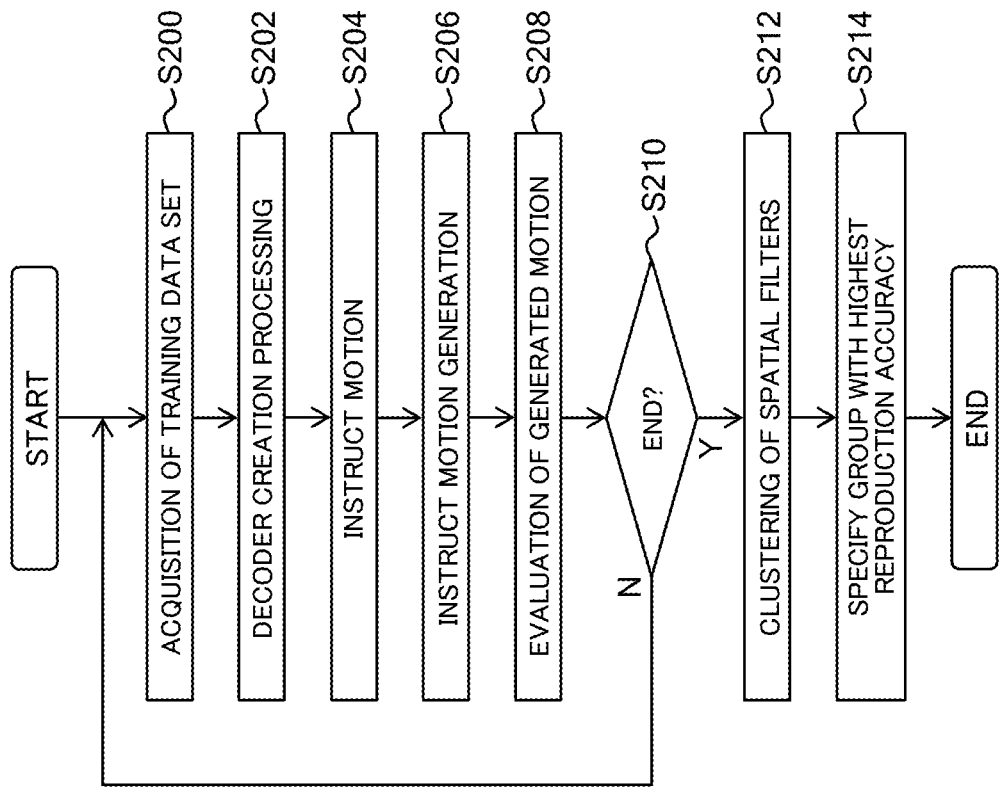
FIG. 6 shows an example of a processing procedure for specifying a group of optimal spatial filters for mastering a target motor pattern.

Next, clustering of spatial filters will be described, using FIG. 6. FIG. 6 shows an example of a processing procedure for clustering spatial filters obtained from a plurality of test subjects, and specifying a group to which a spatial filter suitable for mastering motion belongs (hereinafter, referred to as the optimal group). In the empirical testing discussed below, the findings of (3) below were also obtained, in addition to (1) and (2) above.

(3) A significant difference arises to the degree to which motion is mastered, due to interaction of the type of cerebral activity of each test subject and the state of cerebral activity during motor teaching.

Since the spatial filter that is utilized in decoding extracts a feature amount of an EEG signal, the type of cerebral activity of the test subject appears in the spatial filter. In view of this, the computer 20 according to the present embodiment clusters the spatial filters of the decoders generated for the test subjects, in accordance with the following procedure, and classifies the spatial filters of the test subjects into a plurality of groups. The computer 20 then positions the group to which the type (spatial filter) of cerebral activity of the test subject with the highest degree of mastery of motion belongs as an optimal group that is optimal for mastering the motion, and specifies this optimal group from the plurality of groups obtained by clustering.

Steps S200 and S202

First, in step S200, the computational device 210 acquires the training data set for each of the plurality of test subjects. Acquisition of the training data set of each test subject can be performed similarly to the above step S100. In the following step S202, the computational device 210, similarly to the above step S102, creates an CSP filter and a discriminator that are utilized in the decoder that decodes the cerebral activity of each test subject, based on the training data set of that test subject.

Step S204

In the following step S204, the computational device 210 executes passive teaching of the motor pattern (proprioceptive training) on each test subject, by executing operations for teaching the motor pattern on the force presentation device 80. At this time, the computational device 210 may acquire the EEG signal of each test subject from the brainwave sensor 10, and may decode the acquired EEG signal using the CSP filter and discriminator created in step S202. Also, this teaching of the motor pattern may be performed based on the processing of the steps S104 to S122. The class of cerebral activity of each test subject during motor teaching can thereby be specified. Also, in process of repeated motor teaching, the cerebral activity of each test subject during motor teaching can be guided to be in the "motor imagery" class.

Steps S206 and S208

In the following step S206, the computational device 210 causes the test subject to operate the operation part 82 and reproduce the taught motion himself or herself. In the following step S208, the computational device 210 acquires the position information of the operation part 82 during motion generation from the control module 50, and calculates a reproducibility indicating the extent to which the taught motor pattern is reproduced by the motion generation as an evaluation value of the motion generation. The method of calculating the reproducibility may be set as appropriate according to the embodiment, as long as the extent to which the taught motor pattern was reproduced in the motion generation can be evaluated, and a calculation method according to equation 9 discussed below can be employed, for example.

Step S210

In the following step S210, the computational device 210 determines whether the processing from steps S200 to S208 has been completed for all of the test subjects to be clustered. If the processing from steps S200 to S208 has not been completed for all of the test subjects (N in S210), the computational device 210 repeats the processing from steps S200 to S208 for the test subjects with respect to which the processing has not been completed. On the other hand, if the processing from steps S200 to S208 has been completed for all of the test subjects (Y in S210), the computational device 210 advances the processing to the following step S212.

As a result of the processing from the above steps S200 to S210, the computational device 210 is able to obtain a combination of a CSP filter and a reproducibility of the motor pattern (post-teaching motion result) for all of the test subjects. Note that in the case where the cerebral activity during motor teaching is analyzed as a result of step S204, the computational device 210 may also associate the class ("motor imagery" or "rest state") into which the cerebral activity during motor teaching was classified with the combination of the CSP filter and the reproducibility of the motor pattern.

Step S212

In the following step S212, the computational device 210 classifies the respective CSP filters of the test subjects into a plurality of groups (also referred to as "clusters"), by clustering the CSP filters of the test subjects. A well-known method may be used for the clustering. For example, the computational device 210 defines the distance between CSP filters with the Euclidean distance. The computational device 210 then clusters the CSP filters, such that CSP filters whose distances are close belong to one group. The ward method or the like, for example, can be used in such cluster analysis. The CSP filters of the test subjects are thereby classified into a plurality of groups.

Step S214

In the following step S214, the computational device 210 specifies the optimal group to which the CSP filter of the test subject with the highest degree of mastery of the motor pattern belongs from the plurality of groups, based on the reproducibility of the motor pattern of each test subject. For example, the computational device 210 may perform variance analysis on the reproducibility of each test subject with the output of the decoder and the group of the CSP filter as factors, and specify the group of the CSP filter with the highest degree of improvement in the reproducibility relative to the output of the decoder as the optimal group, based on the result of the variance analysis. The degrees of improvement can be compared using the gradient of the output values or the like, for example. Note that the interaction of the output of the decoder and the CSP filter will also described in the empirical testing discussed below.

The optimal group to which the type of cerebral activity of the test subject with the highest degree of mastery of motion, that is, the type of cerebral activity (spatial filter utilized in decoding) with optimal mastery of the motion pattern to be learned, belongs can thereby be specified. When this optimal group is specified, the computational device 210 ends the processing.

Note that the processing procedure described above is merely an example of the processing procedure for specifying the optimal group, and the respective processing may be changed to the maximum extent possible. Also, with regard to the above processing procedure, steps can be omitted, replaced or added as appropriate, according to the embodiment.

For example, in the example of FIG. 6, as a result of the processing from the above steps S200 to S210 being repeatedly executed, the computational device 210 acquires a combination of the CSP filter of each test subject and the reproducibility of the motor pattern. However, the processing procedure for acquiring this combination need not be limited to such an example. For example, the computational device 210 may acquire the CSP filter of each test subject and the reproducibility of the motor pattern, by applying the processing from steps S202 to S208 to each training data set, after acquiring the training data sets for all of the test subjects.

Also, for example, calculation of the CSP filter of each test subject and the reproducibility of the motor pattern may be performed by another computer. In this case, the computer 20 may acquire the combination of the CSP filter of each test subject and the reproducibility of the motor pattern from another computer via a network, the storage medium 91, or the like.

Utilization of Information on Specified Optimal Group

Figure 7:
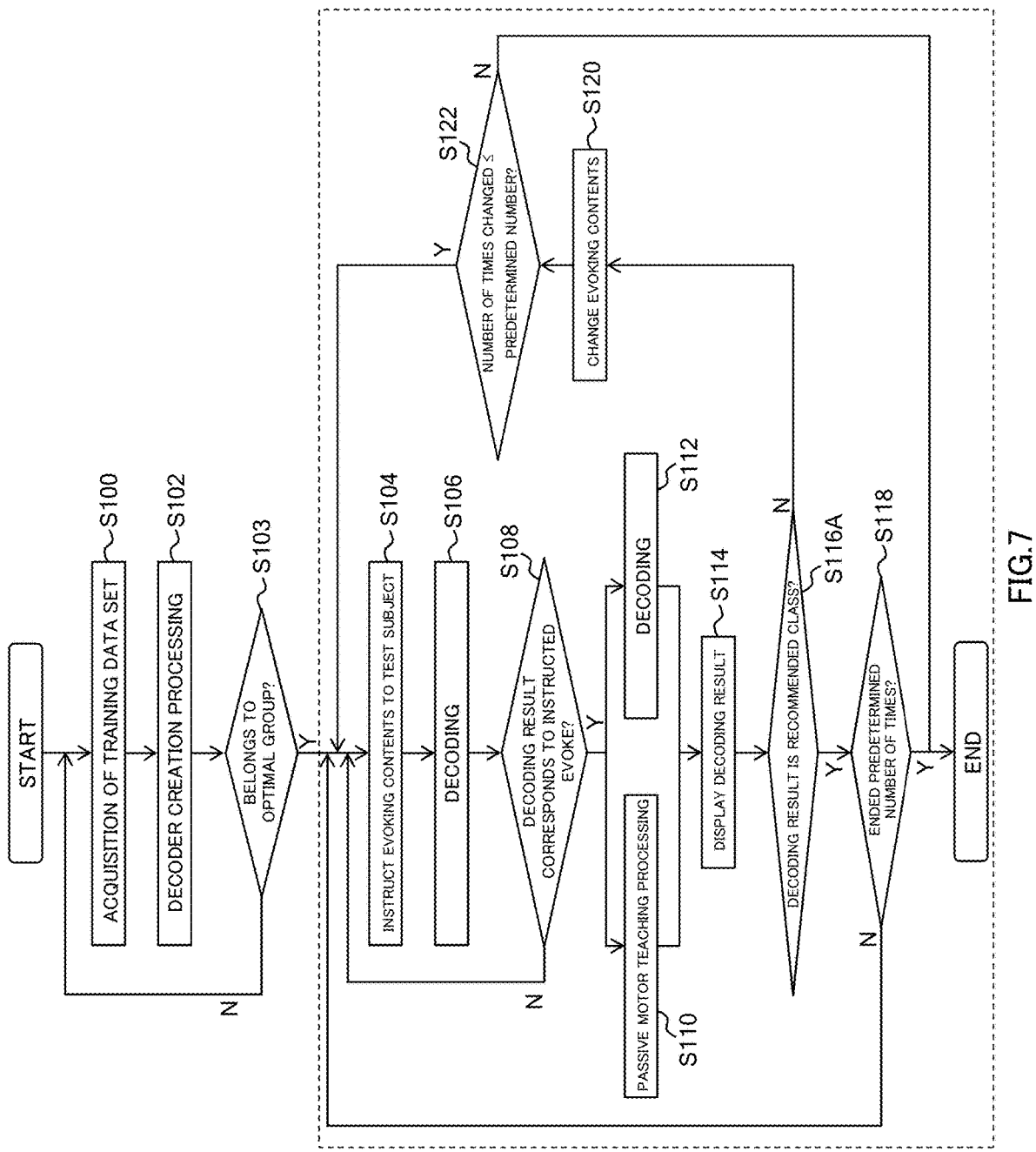
FIG. 7 shows an example of a processing procedure of the motor teaching system in the case where the type of cerebral activity of test subjects is taken into consideration.

Next, a method of utilizing information on the optimal group specified as described above in motor teaching will be described, using FIG. 7. FIG. 7 shows an example of a processing procedure of the motor teaching system 1000 in the case where the type of cerebral activity of the test subject 2 is taken into consideration.

As described above, in the case where the type of cerebral activity of a test subject belongs to the optimal group specified above, that test subject is presumed to be able to efficiently master the target motor pattern. In view of this, the motor teaching system 1000, in the above flow of teaching, as shown in FIG. 7, may prompt the test subject to train, such that the type of cerebral activity of the test subject belongs to the optimal group, that is, such that cerebral activity of the type belonging to the optimal group can be carried out, before starting motor teaching.

Specifically, the computational device 210 of the computer 20 determines whether the CSP filter of the test subject 2 generated in step S102 belongs to the optimal group between steps S102 and S104 (step S103). The method of determining whether the CSP filter of the test subject 2 belongs to the optimal group is set as appropriate depending on the method of clustering employed when the optimal group is specified. For example, the computational device 210 calculates the Euclidean distance between the center of gravity of each group obtained by clustering and the CSP filter of the test subject 2, and specifies groups for which the calculated Euclidean distance is lower than a predetermined threshold. The group to which the CSP filter of the test subject 2 belongs can thereby be specified.

In the case where the CSP filter of the test subject 2 belongs to the optimal group, the computational device 210 teaches the motor pattern to the test subject 2 from the following step S104 onward, assuming that the type of cerebral activity of the test subject 2 is suitable for mastering the target motion. On the other hand, in the case where the CSP filter of the test subject 2 does not belong to the optimal group, the computational device 210 repeats the processing from step S100. That is, the computational device 210 again masters the training data set of the test subject 2, using the brainwave sensor 10. The test subject 2 can thereby be prompted to train so that cerebral activity of the type belonging to the optimal group is carried out.

Note that, in the empirical testing discussed below, test subjects whose type of cerebral activity belonged to an F (Focal) group and whose output of the decoder during motor teaching was large had the highest degree of mastery of the motor pattern. It is assumed, however, that the type of cerebral activity at the time of motor imagery differs depending on the respective test subject. With regard to test subjects whose type of cerebral activity belonged to a NF (Non Focal) group and whose output of the decoder during motor teaching was large, a tendency for the degree of mastery to decrease was evident. With the type of visual motor imagery and kinesthetic motor imagery discussed below, the fact that the change in cerebral activity is reversed and the degree of motor imagery appears as event-related desynchronization or event-related synchronization is envisaged to be a factor. Thus, the degree of mastery of the motor pattern does not necessarily become high when a test subject who carries out cerebral activity of the type belonging to the optimal group carries out motor imagery during motor teaching. That is, the degree of mastery of the motor pattern could possibly be most improved by the test subject who carries out cerebral activity of the type belonging to the optimal group carrying out imagery other than motor imagery (e.g., rest state) during motor teaching.

In view of this, in the process of specifying the optimal group, the computational device 210, in the case where the classified class of the cerebral activity of each test subject during motor teaching is associated with the CSP filter and the reproducibility of the test subject, classifies each test subject belonging to the optimal group for every class of cerebral activity during motor teaching, and compares the reproducibility of the test subjects classified into each class. The computational device 210 may thereby specify the class to which test subjects with a high reproducibility belong, and set the specified class as a recommended class into which to classify the cerebral activity recommended during teaching of the motor pattern. The computational device 210 may also associate the set recommended class with the optimal group.

In this case, the degree of mastery of the motor pattern will not necessarily improve if motor imagery is carried out during motor teaching. Thus, as a result of the above step S103, the computational device 210, in the case where the test subject 2 is prompted to carry out cerebral activity of the type belonging to the optimal group, executes the processing of the following step S116A in place of the above step S116, as shown in FIG. 7. That is, as a result of decoding the EEG signal of the test subject 2 acquired from the brainwave sensor 10 during the period of teaching the motor pattern, the computational device 210 determines whether the cerebral activity of the test subject 2 during the period of teaching the motor pattern is classified into the recommended class associated with the optimal group.

In the case where the cerebral activity of the test subject 2 during the period of teaching the motor pattern is classified into the recommended class associated with the optimal group (Y in S116A), the computational device 210 then advances the processing to the following step S118. On the other hand, in the case where the cerebral activity of the test subject 2 during the period of teaching the motor pattern is not classified into the recommended class associated with the optimal group (N in S116A), the computational device 210 advances the processing to the following step S120. The computational device 210, in steps S104 to S108, can thereby be configured to output the evoking contents to be performed to the test subject 2 prior to teaching of the motor pattern, such that the cerebral activity of the test subject 2 during the period of teaching the motor pattern is classified into the recommended class associated with the optimal group.

Note that, in the above example, a method of repeatedly creating a decoder until the CSP filter selected by the feature selection algorithm belongs to the optimal group was illustrated as the method of providing guidance such that the type of cerebral activity of the test subject belongs to the optimal group. However, the method of guiding the type of cerebral activity of the test subject so as to belong to the optimal group need not be restricted to such an example. For example, if, in step S102, a CSP filter belonging to the optimal group exists among the plurality of CSP filters generated by the CSP algorithm, the computational device 210 may select this CSP filter belonging to the optimal group as the CSP filter to be utilized, rather than implementing selection by the feature selection algorithm. The computational device 210 may then create a decoder utilizing this selected CSP filter. Furthermore, the computational device 210 may repeatedly instruct the test subject to carry out motor imagery between steps S102 and S104, until the output of the generated decoder becomes larger than a threshold. The computational device 210 may then implement the motor teaching from step S104 onward, after the output of the decoder becomes larger than the threshold. The type of cerebral activity of the test subject can also be thereby guided so as to belong to the optimal group.

8. Modifications

Although the embodiment of the present invention has been described in detail above, the foregoing description is, in all respects, merely an illustration of the present invention. Needless to say, various improvements and modifications can be made without departing from the scope of the invention. For example, the following changes can be made. Note that, hereinafter, similar reference signs are used in relation to constituent elements that are similar to the embodiment, and description is omitted as appropriate with regard to points that are similar to the above embodiment. The following modifications can be combined as appropriate.

For example, in the above embodiment, a CSP filter were utilized as the spatial filter, and a linear discriminator that utilizes logistic regression in modeling is utilized as the discriminator. However, the type of spatial filter need not be limited to a CSP filter, and the type of discriminator need not be limited to a linear discriminator that utilizes logistic regression in modeling. The type of spatial filter and discriminator may be selected as appropriate according to the embodiment.

Also, for example, in the above embodiment, information processing such as analysis of cerebral activity, control of motor teaching and specification of the optimal group is performed by the same computational device 210 of the same computer 20. However, the configuration that executes the respective information processing need not be limited to such an example. For example, in the case where the computer 20 is provided with a plurality of computational devices, different computational devices may execute the respective information processing. Also, in the case where the computer 20 is constituted by a plurality of computers, different computers may execute the respective information processing. In this case, the computers may exchange the results of the information processing via a network, a storage medium or the like.

Also, in step S104 of FIG. 5, the computational device 210 instructs predetermined evoking contents regardless of the test subject, and, in the case where cerebral activity during the period of motor teaching is not "motor imagery", changes the evoking contents for instructing, in step S120. However, the method of instructing the evoking contents need not be limited to such an example. For example, a database showing the transition pattern for every test subject 2 may be created in advance. In this case, in step S104, the computational device 210 may determine the evoking contents for instructing to the target test subject 2, with reference to this database.

Also, in the above embodiment, the operation part 82 of the force presentation device 80 guides the motion of the hands of the test subject 2, by moving along the trajectory (circular trajectory) of a predetermined motor pattern, and the test subject 2 thereby passively learns motion in line with the predetermined motor pattern. However, the method of guiding movement of a movable part of the test subject need not be limited to such an example. For example, in the case where the movable part of the test subject is straying from the trajectory of the predetermined motor pattern in this way, the force presentation device 80 may guide the movement of the movable part of the test subject, by feeding back force that returns the movable part of the test subject to the trajectory. Also, in this case, the force presentation device 80 may guide the movement of the movable part of the test subject, by feeding back force in a direction that strays more from the trajectory, rather than return the movable part to that trajectory. Even with these methods, it is possible to allow the test subject to learn the trajectory of a predetermined motor pattern. It is also possible to employ a learning method that is known as "assist-as-needed", which is a control technique that attains target motion as a result of the robot assisting any deficiency in the power of the test subject. Note that, in the above embodiment, a circular trajectory is illustrated as a motor pattern. However, the type of motor pattern need not be limited to a circular trajectory. The motor pattern may be set as appropriate according to the embodiment. In this case, the method of calculating the reproducibility may be determined as appropriate according to the set motor pattern.

9. Empirical Testing

Hereinafter, empirical testing and test results that show the validity of the sequence of the motor teaching by the motor teaching system 1000 as described above.

9.1 Test Conditions (a) Motor teaching robot

The force presentation device shown in FIG. 1 was used in a motor teaching robot. The force presentation device is able to control the position of the handle (operation part), enabling the handle in a state of being held by the test subject to be smoothly moved along a target trajectory on a two-dimensional plane. In this empirical testing, only proprioceptive feedback was given to the test subject, and there was no feedback relating to visual motion.

(b) Test Subjects

The test subjects were 20 right-handed healthy adults.

(c) Feedback to Test Subjects

In this empirical testing, only force feedback was given to the test subjects, in relation to motor teaching. This is because it is conceivable to forget motion that has taken time and effort to learn through force due to being swayed by visual information, when the both force feedback and visual feedback are given, when the test subject generates motion within his or her brain during learning. The size of the target trajectory and a cursor of the target trajectory were displayed on a screen prior to motor teaching, and each test subject was taught the motor pattern to be learned. Neither the size of the target circle nor the cursor of the target trajectory was displayed while the test subject was being moved by the robot (called "Passive Movement: PM"). Similarly, neither the size of the target circle nor the cursor of the target trajectory was displayed while the test subject was generating motion (called "Motor Execution: ME").

(d) Flow of Testing

Figure 8:
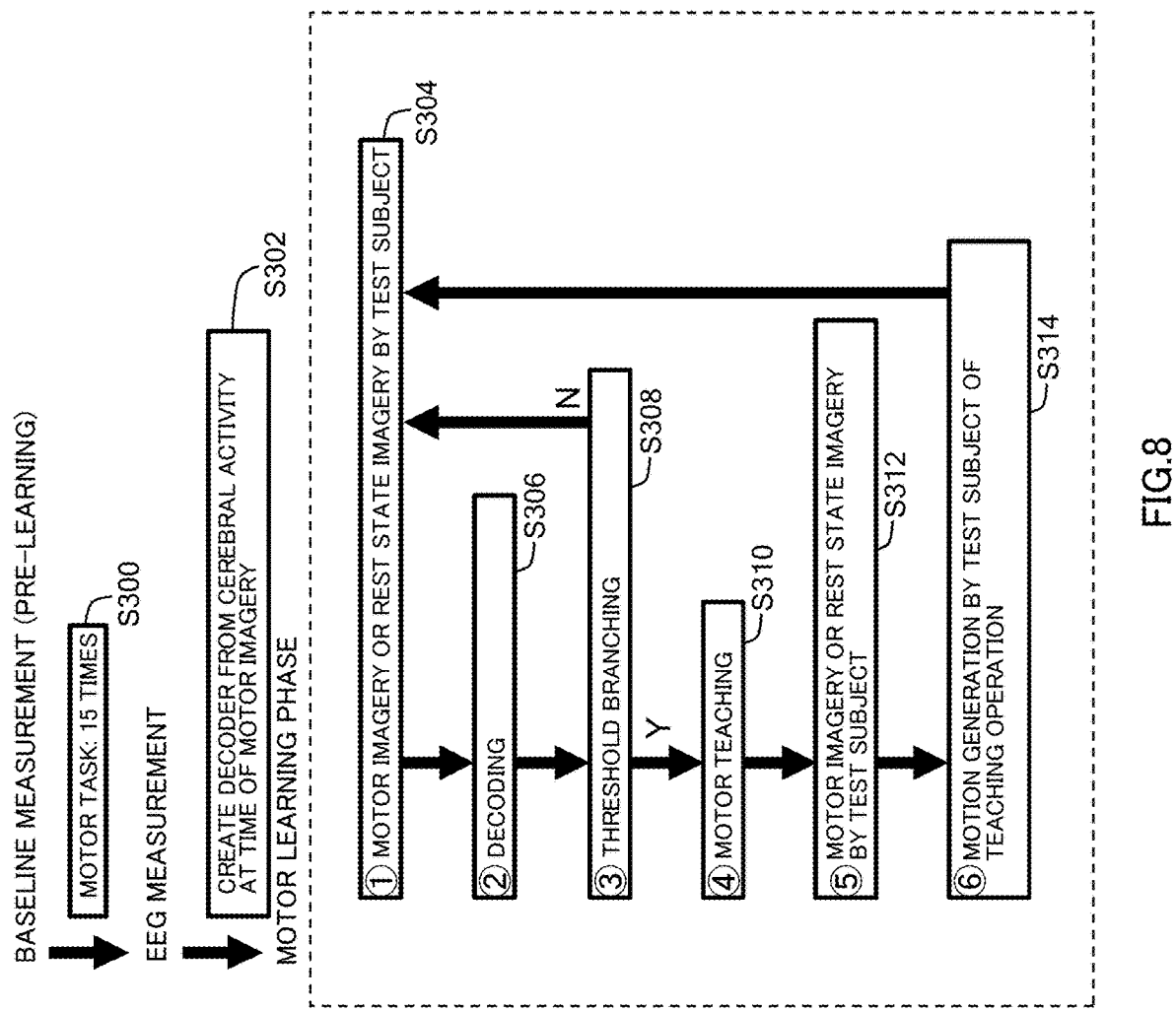
FIG. 8 shows a procedure of empirical testing.

FIG. 8 is a conceptual diagram showing the flow of testing. This empirical testing involves creating the decoder of each test subject, measuring cerebral activity prior to motor teaching and during motor teaching, and evaluating motion generation after motor teaching.

Demonstration of Target Motion and Baseline Measurement

First, in step S300, a two-dimensional target trajectory that traces a circle of 10 cm in radius taking approximately 1.5 seconds to come once round was determined, and the tester performed a demonstration of the target motion 5 times to the test subjects. Thereafter, the test subjects generated target motion continuously for 15 times with the opposite hand to their dominant hand, that is, with their left hand, and measurement of the baseline was performed. The measurement time was set at 5 seconds per iteration. At this time, visual feedback to the test subjects was configured such that it was not possible to know the position of the tips of the fingers.

In this state, it was impossible to judge the quality of the motion. In view of this, the generated motion was evaluated each time and a score out of 100 was fed back to the test subjects after motion generation. The target motion was generated, relying only on the evaluation values, without motor teaching by a robot. The test subjects were instructed to make an effort to obtain a high score.

Creation of Decoder

In the following S302, the decoder that is used in the system was created for every test subject. The test subjects were made to alternately perform 7 seconds of rest state and 5 seconds of motor imagery over 40 repetitions. The brainwaves at this time were measured by a brainwave sensor, and training data sets were collected. A break was taken every 10 repetitions. The time for carrying out motor imagery was set to the same time as baseline measurement time. Therefore, the test subjects were given instruction to imagine, one time, motion carried out when a high score was obtained. No visual feedback was given to the test subjects at this time. Instruction to look at the point of regard (+mark) was given during both the rest state and motor imagery.

In creating the decoder, cross-verification was performed, using EEG signals measured 40 times in sets of 10 times each. Signals of the 7 to 30 Hz frequency bands were filtered, and channels with a high noise level were removed. The above CSP algorithm was applied to the signals after filtering, and a plurality of CSP filters were obtained. Next, CSP filter to be utilized were selected from among the plurality of CSP filters by the feature selection algorithm. Linear discriminant analysis was performed, on the basis of a mean value for 7 seconds for the rest state and a mean value for 5 seconds for motor imagery, and discriminators were created. Note that, for five of the 20 persons, the CSP filter selected by the feature selection algorithm was clearly an error, and thus the CSP filter to be utilized was corrected manually.

Figure 9A:
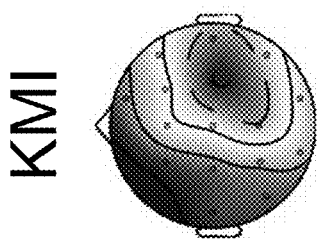
FIG. 9A shows power change at the time of observing the cerebral activity of motor imagery using spatial filters that support kinesthetic motor imagery (KMI).
Figure 9A:
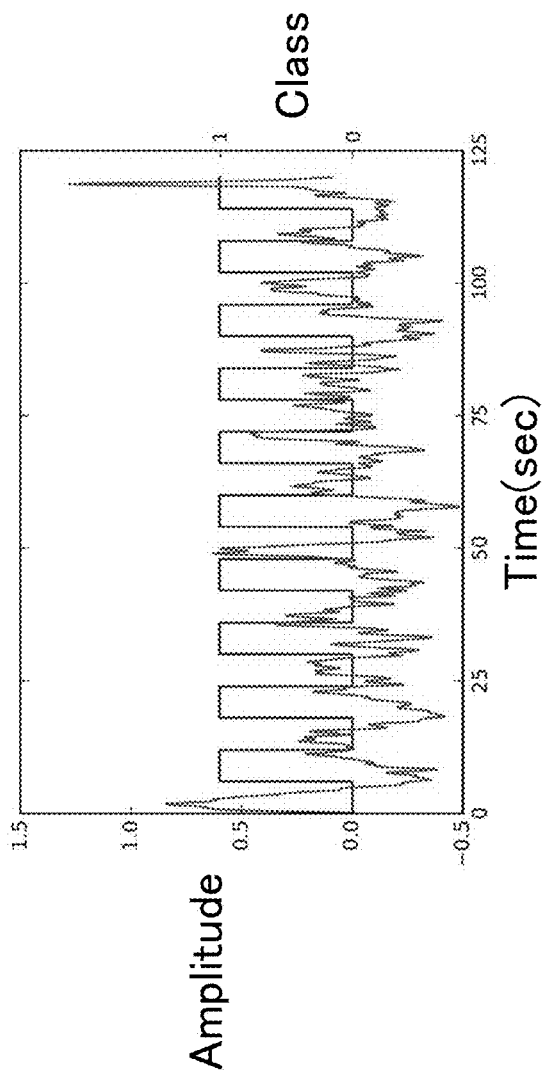
Figure 9B:
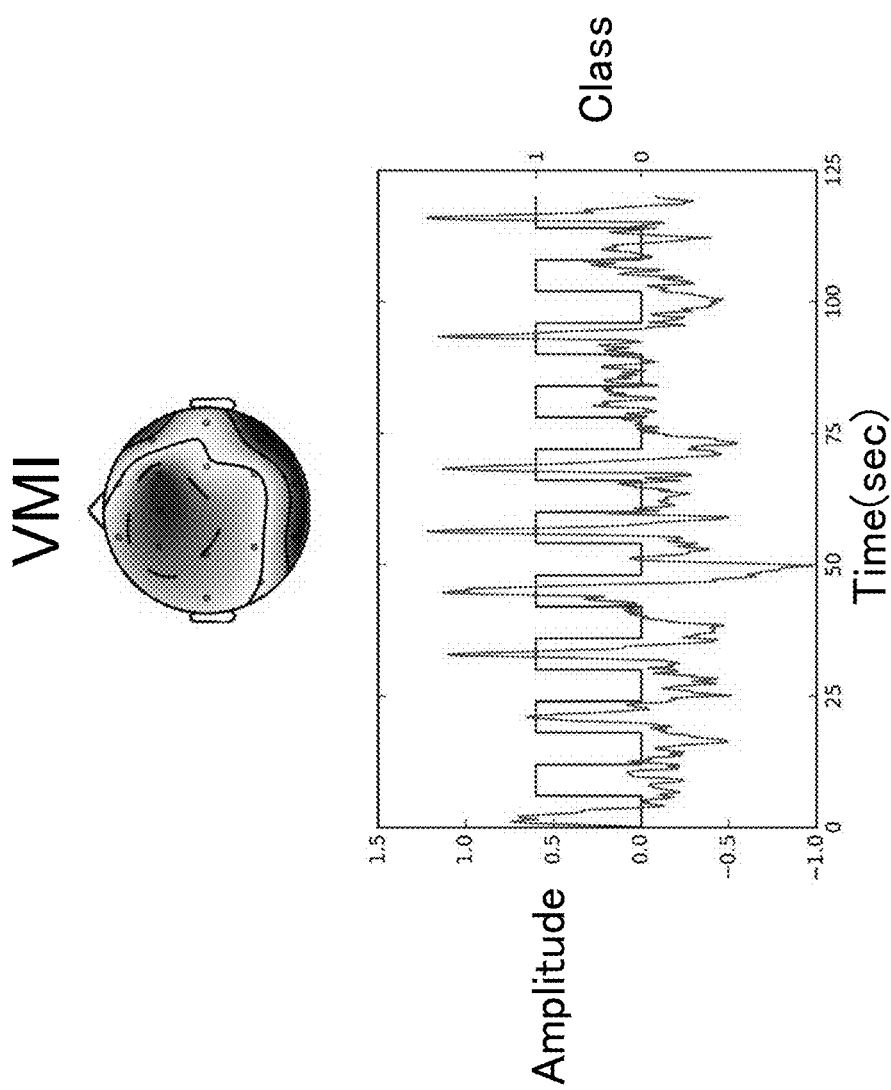
FIG. 9B shows power change at the time of observing the cerebral activity of motor imagery using spatial filters corresponding to visual motor imagery (VMI).

FIGS. 9A and 9B show the change in power at the time that the cerebral activity of motor imagery was observed using the selected CSP filter. Specifically, FIG. 9A shows the change in power at the time that the cerebral activity of the test subjects who carried out kinesthetic motor imagery (KMI) was observed. On the other hand, FIG. 9B shows the change in power at the time that the cerebral activity of the test subjects who performed visual motor imagery (VMI) was observed.

Generally, two types of motor imagery are known. The first type is kinesthetic motor imagery (KMI) in which variation in the power (ERD/ERS) of α and β bands in a sensorimotor area is seen, in response to first-person motor imagery. Here, ERD is event-related desynchronization, and ERS is event-related synchronization.

The second type is visual motor imagery (VMI) in which activity in the visual area is seen, even in the case of third-person motor imagery or no visual input. In a first study of the empirical testing mentioned later, only CSP filters respectively corresponding kinesthetic motor imagery (KMI) and visual motor imagery (VMI), as shown in FIGS. 9A and 9B, are targeted.

Motor Learning Phase

First Iteration of Cerebral Status Control

Returning to FIG. 8, a motor learning phase was implemented after creating the decoders. First, in this empirical testing, before motion was passively taught by a robot, the test subjects were made to perform operation of the cerebral status using the system for 5 seconds (S304-S308).

Here, the condition for causing the rest state was referred to as a first test condition, and the condition for causing motor imagery was referred to as a second test condition. Ten test subjects were randomly allocated to each test condition.

The brainwave signals of the test subjects where passed through the decoders created in step S202, such that test subjects could check whether their own cerebral status was the rest state or motor imagery, and the decoding results were visually fed back with the bar on the screen (S306). The test subjects were, however, instructed that they were in the rest state when the bar was close to "0" and carrying out motor imagery when the bar was close to "100", without being informed of the threshold dividing the rest state and motor imagery. Also, the test subjects were made to control their cerebral status while viewing the point of regard where possible, and instructed to refer to the screen to the extent that the bar was in their field of view. The subsequent sequence was changed, according to the result of this control of the cerebral status.

If the mean value of the result of the test subjects performing 5 seconds of brainwave discrimination was less than (first test condition)/greater than (second test condition) a threshold (Y in S308), the sequence subsequent to motor teaching was executed (S310). On the other hand, if the threshold was not cleared (N in S308), the motor learning phase was performed again from control of the cerebral status in step S204, after inserting 7 seconds of the rest state (bar hidden).

Note that after being made to perform the operation of the cerebral status of the target test condition, each test subject was made to perform the operation of the cerebral status of the other test condition. That is, the test subjects who were made to perform the operation of the cerebral status of the first test condition were subsequently made to perform the operation of the cerebral status of the second test condition, and the test subjects who were made to perform the operation of the cerebral status of the second test condition were subsequently made to perform the operation of the cerebral status of the first test condition. The data of the subsequent operation was, however, excluded from being used in other studies that excluded study of transition patterns.

Motion Teaching by Robot

After clearing the threshold with above bar control of the cerebral status (Y in S308), teaching of target motion by robot was immediately started (S310). The robotic arm was PID controlled, and the hand of the test subject was passively moved. For safety reasons, the robot was configured to stop, in the case where the test subject applied force greater than or equal to a certain level to the robot. At this time, the test subjects could not visually see the size of the circle to be drawn, nor could they see the movement of the robot (FIG. 3). Accordingly, in this step S310, proprioceptive training without visual influence was implemented.

At this time, instruction was given to the test subjects to remember position/speed and movement so as to be subsequently reproduce the motion accurately. The test subjects held the handle portion (operation part) of the robot, and a jig for supporting the weight of arms such as an armrest was not used.

Second Iteration of Cerebral Status Control

Soon after the motor teaching by robot had finished, cerebral status control was performed for the second time (S312). However, threshold evaluation was not provided by bar control in this step S312, and the processing transitioned to the following step S314 even if the threshold was not cleared. The test subjects were, however, not informed that there was no threshold evaluation in this step S312. The test subjects were made to perform bar control so as to respectively approach the cerebral status of the first test condition and the second test condition.

Motion Recreation by Test Subject and Measurement by Robot

The test subjects were instructed to move the handle portion of the robot that performed motor teaching in the same manner as the taught motor pattern, and the trajectory of the handle portion that was moved by the test subjects was measured (S314). At this time, the test subjects controlled the robot so as to be able to reproduce the motion with low resistance, while hardly feeling the weight of the robot. Also, at this time, the test subjects were prevented from seeing the position of their hand by the screen. After reproducing the motion, the test subjects were given a reproducibility score out of 100.

Number of Iterations

The above flow from S304 to S314 was performed repeatedly. The test subjects received motor teaching by robot at least 15 times, and were given the opportunity to reproduce the motion 15 times.

A break of around 1 to 2 minutes was taken as needed every 15 tries at condition switching by the cerebral status control of S304 to S308. The overall test time and time interval of motor learning differ depending on the ability or inability of the test subjects to perform cerebral status control. Note that the time interval of motor learning and motion reproduction is always constant at 5 seconds.

Figure 10:
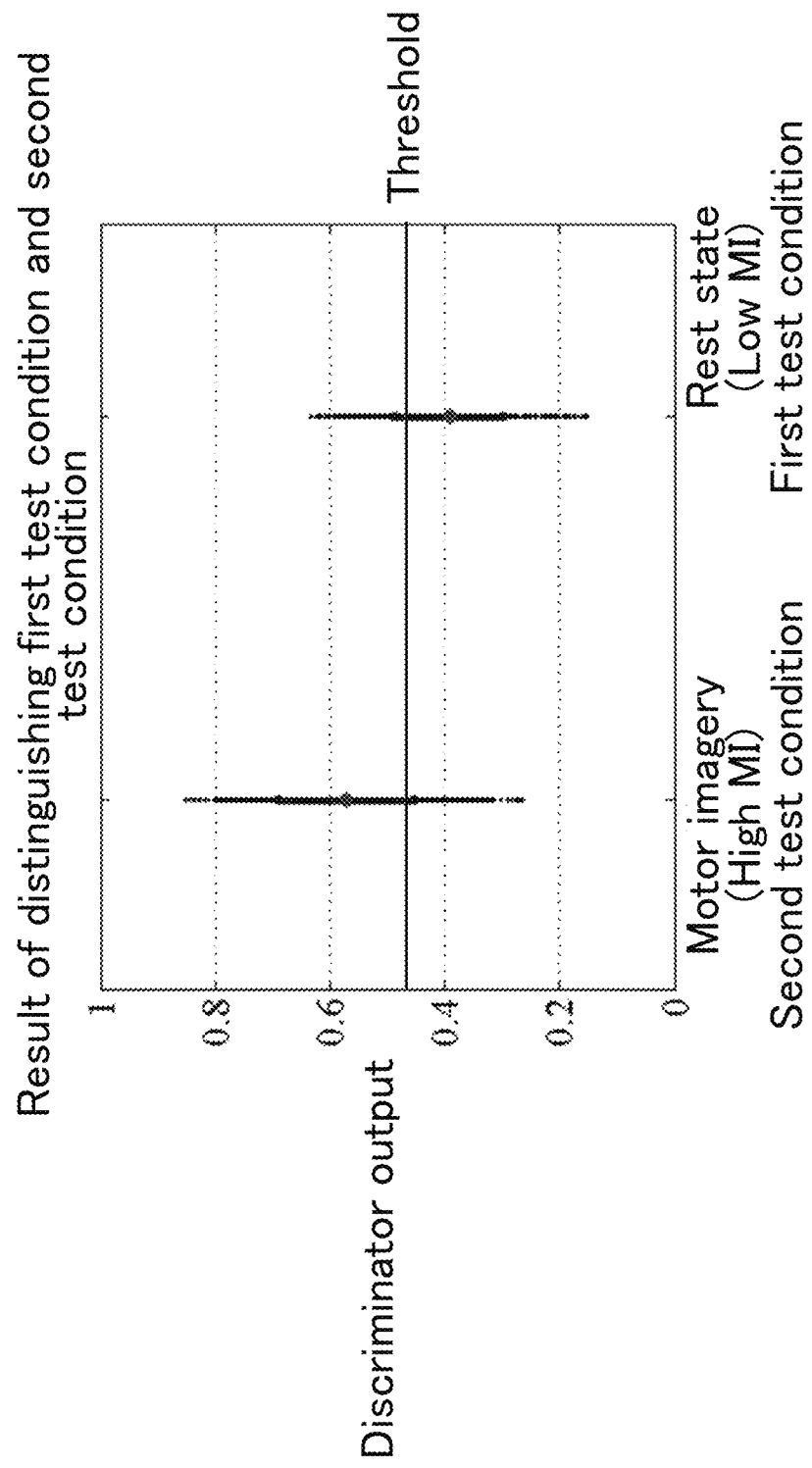
FIG. 10 shows the output of a discriminator in a first test condition and a second test condition of a given test subject.

(e) Decoder Discrimination Results by Cerebral Status Control of Test Conditions FIG. 10 shows the output of a discriminator at the time that a certain test subject is made to perform the operation of the cerebral status of the first test condition and the operation of the cerebral status of the second test condition. As described above, in the first test condition, the test subject was made to control the cerebral status to be in the rest state, and, in the second test condition, the test subject was made to control the cerebral status to be motor imagery. As shown in FIG. 10, in the control of the second test condition, the mean value was greater than the threshold, and, in the control of the first test condition, the mean value was less than the threshold. Thus, the decoder was correctly created, and the test subject knew that operation of the bar, that is, control of the cerebral status has been successfully performed.

Figure 11:
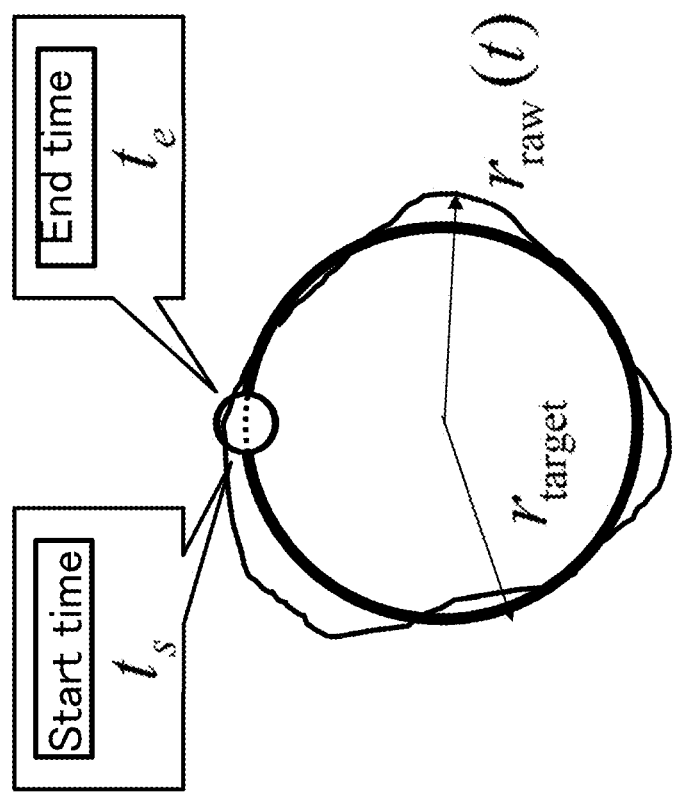
FIG. 11 is a conceptual diagram for describing error between a target trajectory and a trajectory reproduced by a test subject.

(f) Equation of Error with Respect to Target Trajectory of Motion Reproduction Result FIG. 11 is a conceptual diagram for describing error between the target trajectory and the trajectory reproduced by the test subject. Motion reproduced by the test subjects was evaluated on the basis of the trajectory of the target motion. The time period ($t=t_e$) from the point in time ($t=t_s$) at which the target trajectory leaves a reference start circle (3 cm radius) from the start position at 12 o'clock until the target trajectory enters the reference start circle again was set as an evaluation period. The evaluation period was approximately 1.5 seconds. The mean error and the standard error with respect to the target trajectory (dotted line in FIG. 11) for 1.5 seconds after the point in time at which the hand trajectory (solid line in FIG. 11) reproduced by the test subject leaves the reference start circle from the start position at 12 o'clock were calculated in accordance with the following equations. The calculated mean error was then converted into a score out of 100 in accordance with a predetermined equation.

$$E(t)=|\sqrt{x_{raw}^2(t)+y_{raw}^2(t)}-r_{target}|=|r_{raw}(t)-r_{target}| \quad \text{Equation 9}$$

Mean Error $$\text{mean}\left(\sum_{t=t_s}^{t_e} E(t)\right)$$

Note that the mean error is referred to below as an "error".

(g) Cerebral Activity State and Learning Result During Motor Teaching

FIG. 12 is a conceptual diagram for describing the evoking contents that are instructed to the test subjects before and after motor teaching in the process of the above steps S304 to S314. As shown in FIG. 12, in the above testing, the test subject designated to the first test condition was instructed to control the cerebral status to "rest state" before and after motor teaching. On the other hand, the test subject designated to the second test condition was instructed to control the cerebral status to "motor imagery" before and after motor teaching. Each test subject was presented with whether the cerebral activity was decoded by the decoder as the rest state or the motor imagery state, before and after motor teaching, using the bar on the screen.

The cerebral activity of the test subject during motor teaching was then discriminated by the decoder. During motor teaching, the display "Please remember the movement of the robot", which is a uniform instruction, was performed on the screen with respect to the test subject. However, it is evident that, despite having performed such a display, the result of decoding the cerebral activity during motor teaching is divided into the two classes of motor imagery and rest state. Hereinafter, the test results will be described.

9.2 First Study

First, it was studied whether the cerebral activity during motor teaching affects mastering of motion.

Result of Discriminating Brainwaves at Time of Motor Teaching

First, the class of cerebral activity of each test subject during motor teaching was classified, based on the result of decoding the brainwave signal acquired during motor teaching. That is, a brainwave signal of approximately 2 seconds when motor teaching by robot (Passive Movement: PM) is being performed was decoded by the decoder created for every test subject. In the case where the output of the decoder was low compared with the threshold of the discrimination probability of each test subject, the cerebral activity of the test subject during motor teaching is assumed to be in the rest state, and such a test subject is classified into a "Low group". On the other hand, in the case where the output of the decoder is higher than the threshold, the cerebral activity of the test subject during motor teaching is assumed to be motor imagery, and such a test subject is classified into a "High group".

Figure 13A:
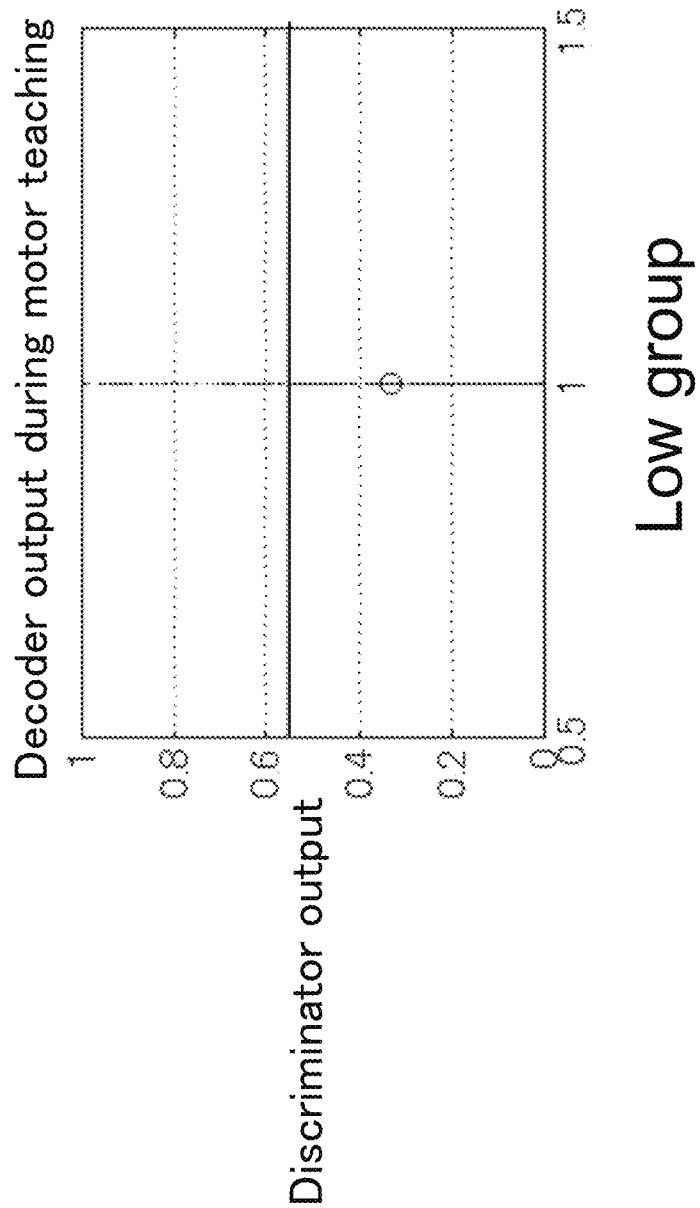
FIG. 13A shows the output of a decoder during motor teaching of a typical test subject in a group in which cerebral activity during motor teaching was in a rest state (rest class).
Figure 13B:
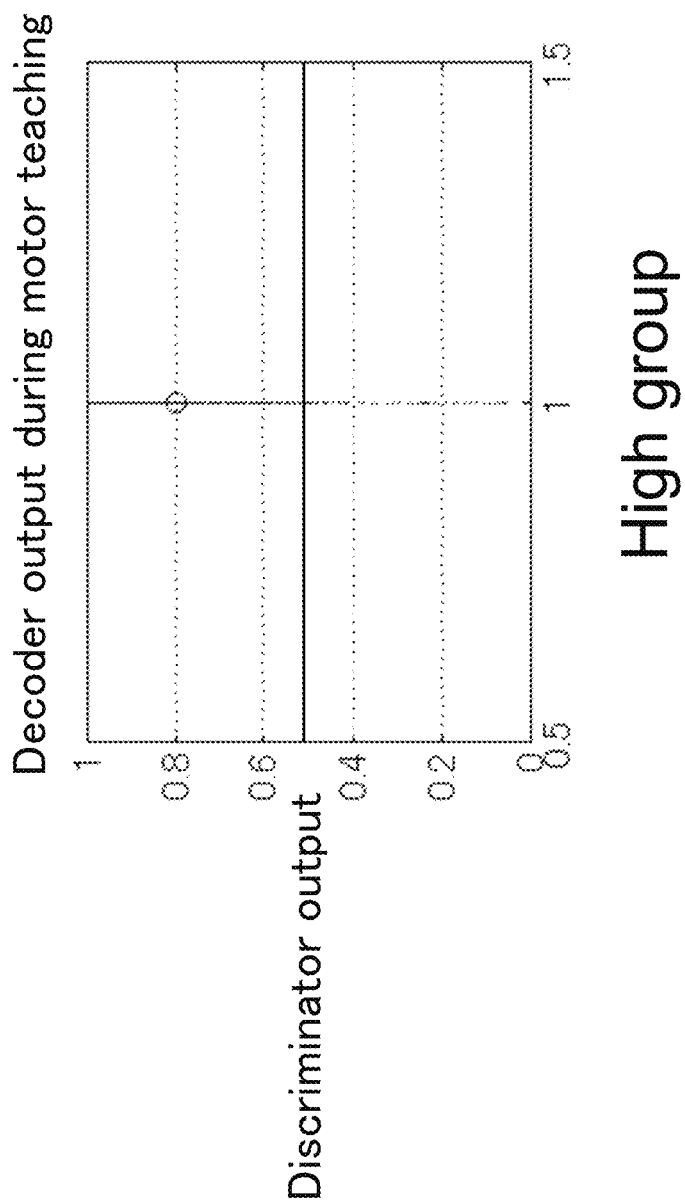
FIG. 13B shows the output of a decoder during motor teaching of a typical test subject in a group in which cerebral activity during motor teaching was in a motor imagery state (motor imagery class).

FIG. 13A shows the output of the decoder of a typical test subject of the rest state class (Low group) during motor teaching. FIG. 13B shows the output of the decoder of a typical test subject of the motor imagery class (High group) during motor teaching. From the results shown in FIG. 13A and FIG. 13B, it is evident that the result of decoding the cerebral activity during motor teaching is divided into the two classes of motor imagery and rest state, as described above.

Figure 14:
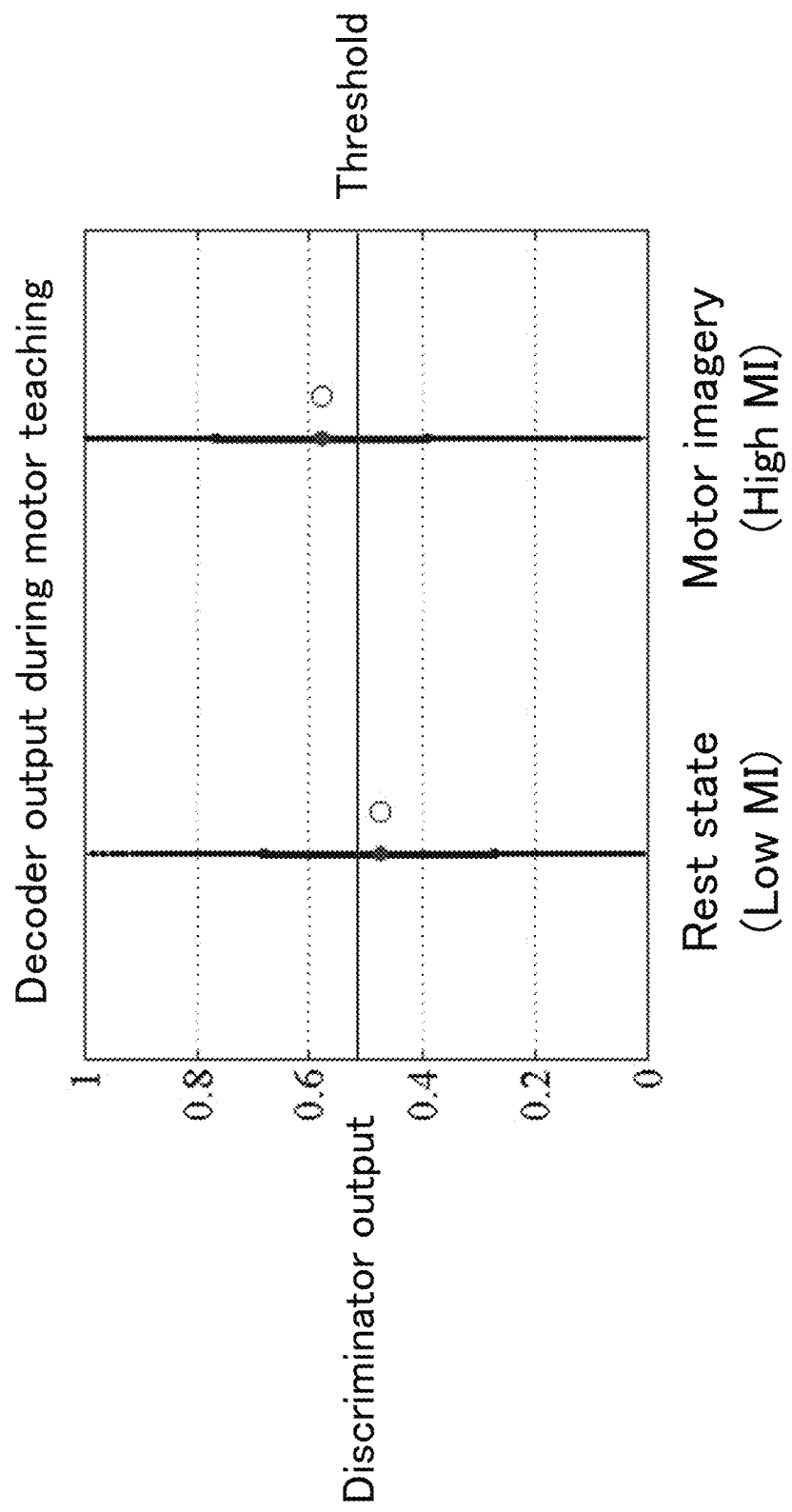
FIG. 14 shows the output of a decoder that is obtained during motor teaching from test subjects belonging respectively to a group in the rest state (Low group: 9 persons) and a group in the motor imagery state (High group: 11 persons).

Also, FIG. 14 shows the output of the decoders of the test subjects belonging to the rest state class (Low group: 9 persons) and the motor imagery class (High group: 11 persons) during motor teaching. The mean output of each group was divided above and below to the mean threshold (solid line) of the 20 persons. Also, Welch's t-test showed that both groups differ significantly ($P<0.05$). It is also evident from this result that the result of decoding the cerebral activity during motor teaching is divided into the two classes of motor imagery and rest state.

Motor Learning Result

Next, it was studied whether a difference arises in motor learning with regard to the classes. First, the mean value of errors of the trajectory of motion when the individual test subjects performed the motion 15 time in baseline measurement (denoted as "baseline") was calculated as the mean error. Next, error in the trajectory of motion when motion reproduction was performed during the motor learning phase (denoted as "motion generation") was calculated for every motion reproduction (15 times). The difference between the error of the motion reproductions of each test subject and the mean error at the time of baseline measurement was then calculated, and the mean value of calculated differences was calculated as the motion result. Thus, it is shown that motion reproduction (motion generation) was performed more accurately as the calculated value decreased.

Figure 15A:
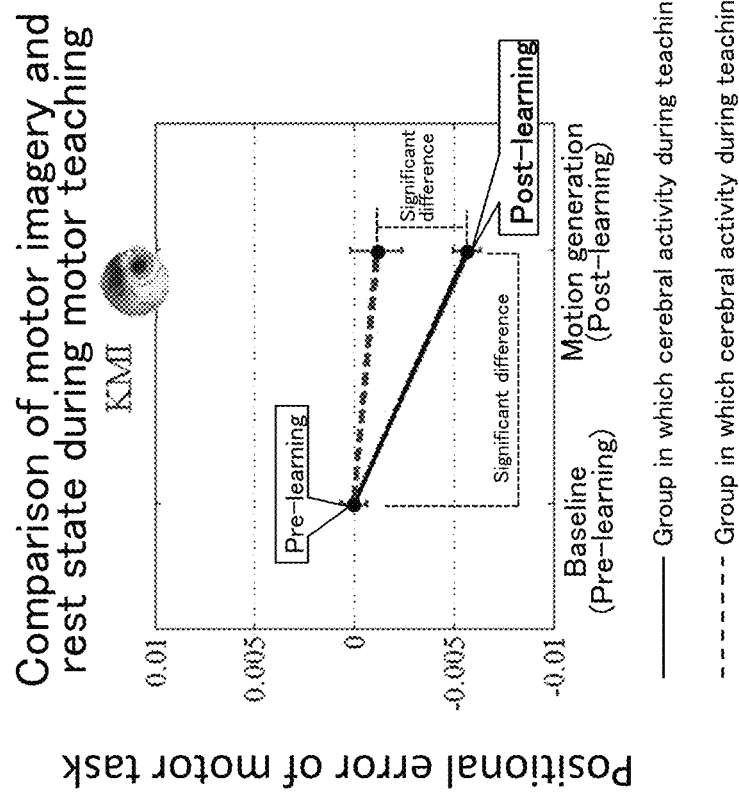
FIG. 15A shows the relationship between the state of cerebral activity during motor teaching of a test subject who performs kinesthetic motor imagery as motor imagery and the mean positional error of motion reproduction (reproducibility).
Figure 15B:
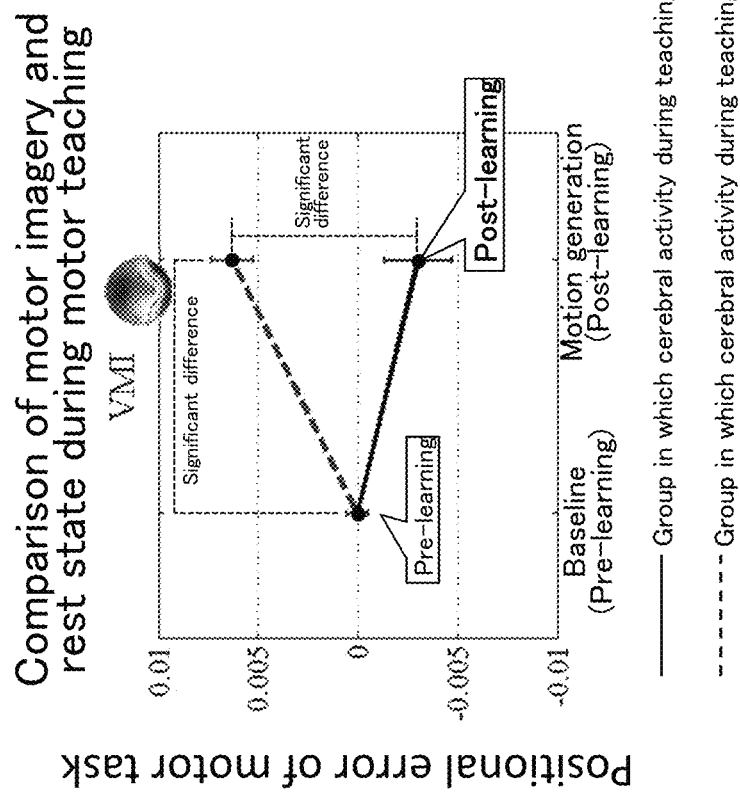
FIG. 15B shows the relationship between the state of cerebral activity during motor teaching of a test subject who performs visual motor imagery as motor imagery and the mean positional error of motion reproduction (reproducibility).

FIGS. 15A and 15B show the relationship between the calculation result, that is, the state of cerebral activity during motor teaching, and the mean positional error of motion generation. Specifically, FIG. 15A shows the relationship between the state of cerebral activity during motor teaching of a test subject who performs kinesthetic motor imagery (KMI) as motor imagery and the mean positional error of motion reproduction (reproducibility). On the other hand, FIG. 15B shows the relationship between the state of cerebral activity during motor teaching of a test subject who performs visual motor imagery (VMI) as motor imagery and the mean positional error of motion reproduction (reproducibility). When the result at the time of motion reproduction falls further below the baseline relative to the vertical axis, the error between the reproduced motion and the target motion will have decreased and learning was successfully performed.

It is evident that, for both of the groups KMI and VMI, the error between reproduced motion and target motion decreases more for the test subjects whose cerebral activity during motor teaching was classified into "motor imagery" than the test subjects classified into the "rest state". Also, Welch's t-test showed that the results of both groups differed significantly (P<0.05). It was obtained the findings of (1) above from the above results.

9.3 Second Study

Secondly, the relationship between the cerebral activity prior to motor teaching and the cerebral activity during teaching was studied. As described above, teaching of motion was performed on each test subject with both test conditions. The transition patterns of the cerebral activity of the test subjects were then classified, based on the result of decoding the cerebral activity during motor teaching with each test condition. FIG. 13 shows the results.

FIG. 13 shows the relationship (transition pattern) between the state of cerebral activity prior to teaching and the state of cerebral activity during teaching. As shown in FIG. 13, it is evident that the relationship between the state of cerebral activity prior to teaching and the state of cerebral activity during teaching is divided into at least the following four transition patterns.

1) Transition Pattern A (Transition Patterns of (A) Above)

The transition pattern A is a group in which, when the state of cerebral activity prior to teaching is "motor imagery (High (MI))", the state of cerebral activity during teaching is also "motor imagery (MI)" state, and when the state of cerebral activity prior to teaching is "rest", the state of cerebral activity during teaching is also "rest (Low)". Six of the 20 people corresponded to this transition patterns A.

2) Transition Pattern B (Transition Pattern of (B) Above)

This is a group in which, when the state of cerebral activity prior to teaching is in the "motor imagery" state, the state of cerebral activity during teaching is in the "rest" state, and when the state of cerebral activity prior to teaching is in the "rest" state, the state of cerebral activity during teaching is in the "motor imagery" state. Two of the 20 people corresponded to this transition pattern B.

3) Transition Pattern C (Transition Pattern of (C) Above)

This is a group in which, when the state of cerebral activity prior to teaching is in the "motor imagery" state, the state of cerebral activity during teaching is also in the "motor imagery" state, and also when the state of cerebral activity prior to teaching is in the "rest" state, the state of cerebral activity during teaching is also in the "motor imagery" state. Six of the 20 people corresponded to this transition pattern C.

4) Transition Pattern D (Transition Pattern of (D) Above)

This is a group in which, when the state of cerebral activity prior to teaching is in the "motor imagery" state, the state of cerebral activity during teaching is also in the "rest" state, and also when the state of cerebral activity prior to teaching is in the "rest" state, the state of cerebral activity during teaching is also in the "rest" state. Six of the 20 people corresponded to this transition pattern D.

It was obtained the findings of (2) above from the above results. Also, when the results of FIGS. 15A and 15B are combined, the cerebral activity of the test subject can be changed to the "motor imagery" state during motor teaching, when the transition pattern of the cerebral activity of the test subject is any of the transition pattern A, the transition pattern B or the transition pattern C, and thus it is surmised that motor learning by the motor teaching system 1000 is effective. In view of this, in the motor teaching system 1000 according to the embodiment, the state of cerebral activity during motor teaching is guided to be in the "motor imagery" state, in a procedure such as shown in the flowchart of FIG. 5.

9.4 Third Study

Figure 17A:
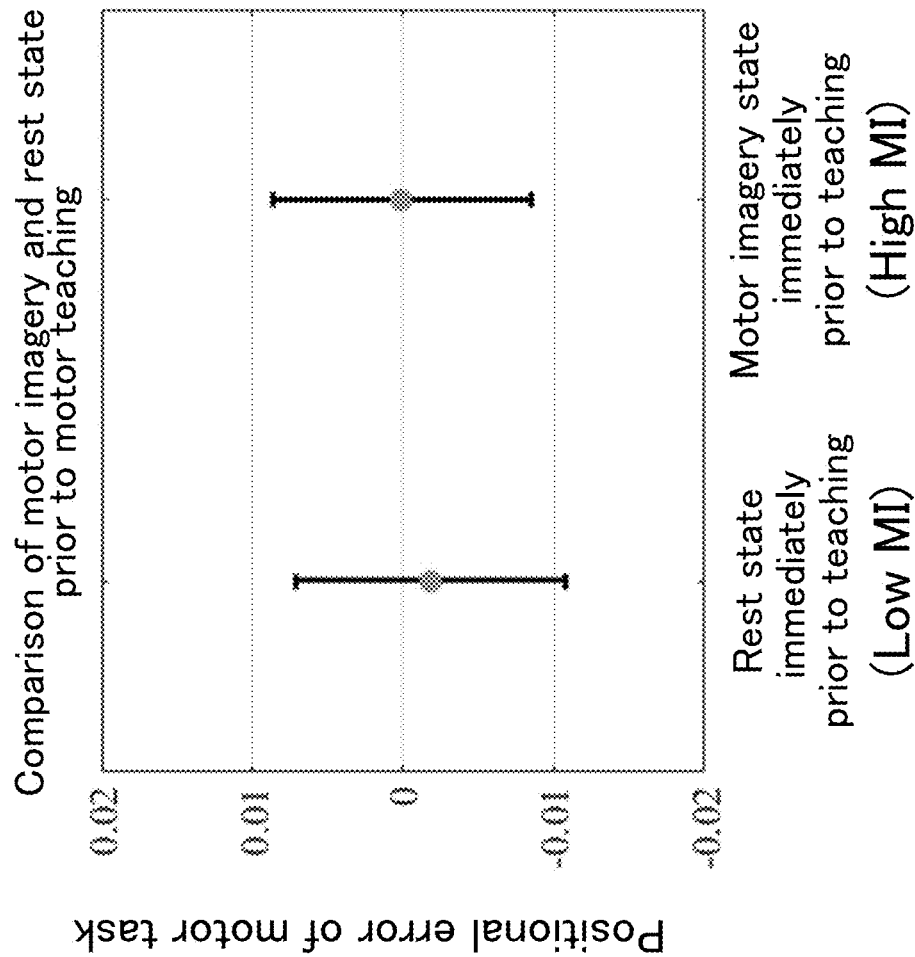
FIG. 17A shows the relationship between the state of cerebral activity prior to motor teaching of 15 test subjects whose spatial filters where selected by a feature selection algorithm and the mean positional error of motion reproduction (reproducibility).

Thirdly, the relationship between the cerebral activity prior to motor teaching and the cerebral activity during teaching was studied again, after excluding the data of the five people who manually selected the CSP filter. First, motion results were calculated for each test subject, as described above. Next, the 15 test subjects were classified, using the two classes of the state of cerebral activity prior to motor teaching. The mean value of motion results was then calculated for every class. FIG. 17A shows the results. That is, FIG. 17A shows the relationship between the state of cerebral activity prior to motor teaching of 15 test subjects for which selection of the CSP filter was performed by the feature selection algorithm and the mean positional error of motion reproduction (reproducibility).

Figure 17B:
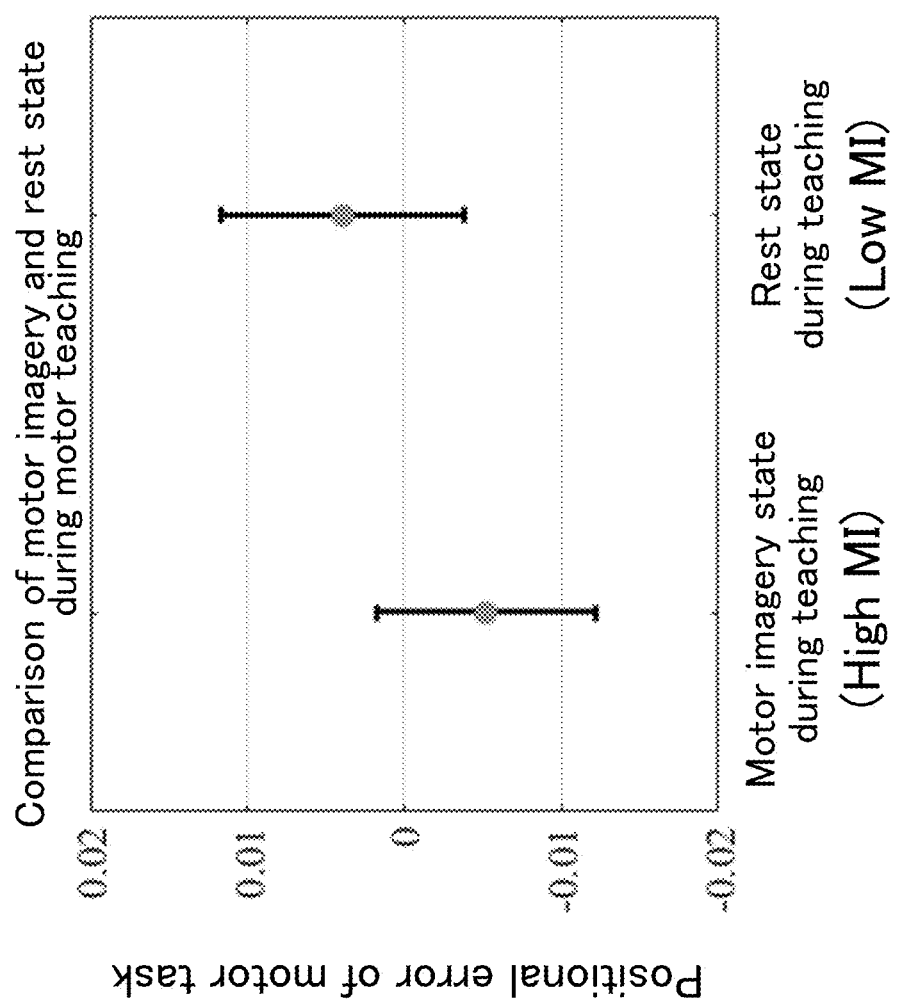
FIG. 17B shows the relationship between the state of cerebral activity during motor teaching of 15 test subjects whose spatial filters where selected by a feature selection algorithm and the mean positional error of motion reproduction (reproducibility).

Next, the 15 test subjects were classified, using the two classes of the state of cerebral activity during motor teaching. The mean value of the motion results was then calculated for every class. FIG. 17B shows the results. That is, FIG. 17B shows the relationship between the state of cerebral activity during motor teaching of 15 test subjects for which selection of the CSP filter was performed by the feature selection algorithm and the mean positional error of motion reproduction (reproducibility).

The t-test showed that there was no significant difference between the two groups shown in FIG. 17A (P=0.7). On the other hand, the t-test showed that there is a significant difference between two groups shown in FIG. 17B (P=0.034). That is, it is evident that, as shown in FIG. 17B, the degree of mastery of the target motor pattern significantly improves when the cerebral activity is in the "motor imagery" state during motor teaching. Even when data is narrowed down to the 15 test subjects for which the CSP filter was selected with the feature selection algorithm, it is evident that the findings of (1) above are correct.

9.5 Fourth Study

Fourthly, it was studied whether the type of cerebral activity of the test subject and the state of cerebral activity during motor teaching could act on each other. First, in order to group types of cerebral activity of the test subjects, clustering of the CSP filters of the test subjects was performed for the 15 test subjects for which selection of the CSP filter was performed by the feature selection algorithm. The distance between CSP filters was defined by the Euclidean distance. Also, the ward system was used in clustering.

Figure 18:
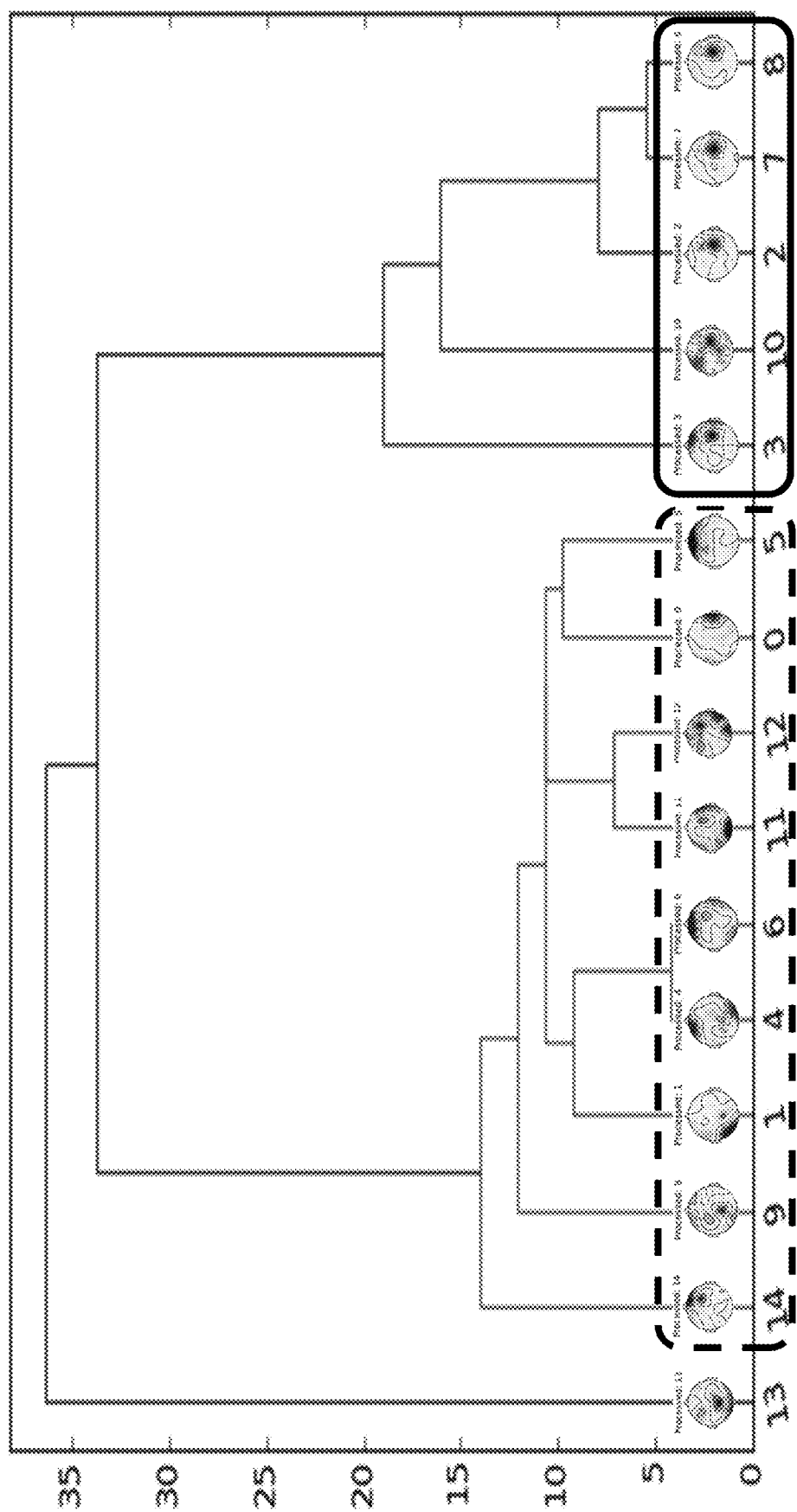
FIG. 18 shows the result of clustering the spatial filters of the 15 test subjects.

FIG. 18 shows the result of having clustered the CSP filters of the 15 test subjects. In the result of the clustering shown in FIG. 18, the CSP filter of the test subject "13" is excluded, and the CSP filters of the remaining 14 test subjects are classified into two groups. Specifically, the CSP filters were classified into a group of CSP filters in which the cerebral activity is concentrated on the vicinity of M1 (hereinafter, also referred to as the "F (Focal) group"), and a group (hereinafter, also referred to as the "NF (Not-focal) group") of CSP filters in which cerebral activity is not concentrated on the vicinity of M1. There were five test subjects who belonged to the F group, and nine test subjects who belonging to the NF group. Note that the types of cerebral activity can be visualized as a CSP map, by associating each weight of a CSP filter with a cerebral map. The CSP map of each test subject is disposed in the leaves of the tree structure shown in FIG. 18.

Next, variance analysis that took the following factors into consideration was performed, with regard to the reproducibility of the motion of each test subject.

Factor A: type of CSP filter (F group, NF group)
Factor B: result of decoding brainwave signal acquired during motor teaching
Random effect: state of cerebral activity during motor teaching (whether "motor imagery" or "rest state")

As a result, it was evident that in the case where the groups of CSP filters are not distinguished, motion results improve in the case the state of cerebral activity during motor teaching is "motor imagery" (FIG. 17B), but that a significant difference arises in the degree of improvement in the motion results between the case where the CSP filter belongs to F group and the case where the CSP filter belongs to the NF group (P=0.042). It was thereby obtained the findings of (3) above. Note that, in this study, the greatest improvement in motion results was seen, in the case where the test subjects who carried out cerebral activity of the type of the F group performed "motor imagery" during motor teaching. Thereby, with regard to the motion of drawing a circle, the most efficient mastery is inferred to be possible by setting the F group as the optimal group and setting the motor imagery class as the recommended class. On the other hand, a tendency was seen for the degree of mastery to conversely decrease during teaching, with regard to test subjects with respect to which the type of cerebral activity belonged to the NF (Non Focal) group and the output of the decoder was large. It is supposed that one factor is that, depending on the type of kinesthetic motor imagery and visual motor imagery, the increase/decrease in cerebral activity is reversed and the degree of motor imagery appears as event-related desynchronization or event-related synchronization. Thus, it is supposed that the degree of mastery of the motor pattern does not necessarily increase when the test subject who carries out cerebral activity of the type belonging to the optimal group performs motor imagery during motor teaching. That is, it is supposed that the degree of mastery of the motor pattern is most likely improved by a test subject who carries out cerebral activity of the type belonging to the optimal group performing imagery other than motor imagery (e.g., rest state) during motor teaching. Note that, in the case where, when selecting an CSP filter to be used in the decoder, a CSP filter belonging to the F group is included in a plurality of CSP filters generated with the CSP algorithm, it can be expected to be able to master motor imagery with respect to which an improvement in motor accuracy can be expected, by selecting this CSP filter even when the contribution is small and implementing operation training of the decoder itself. Note that the possibility of operation training of the decoder itself is disclosed in the following Known Literature 6, for example.

Known Literature 6: ERD-Based Online Brain? Machine Interfaces (BMI) in the Context of Neurorehabilitation: Optimizing BMI Learning and Performance 10. Other Matters Note that embodiments disclosed herein are illustrations of configurations for specifically carrying out the present invention, and do not restrict the technical scope of the present invention. The technical scope of the invention is indicated by the claims rather than by the description of the embodiments, and changes which come within the meaning and range of equivalency of the claims are intended to be embraced therein.

REFERENCE SIGNS LIST

2 Test subject
10 Brainwave sensor
12 Signal acquisition module
20 Computer
30 Training control unit
40 Cerebral activity analysis unit
50 Control module
70 Projector
80 Force presentation device
82 Operation part
202 External interface
210 Computational device
212 Storage device
402 Filter processing unit
404 Decoder
406 Feature amount extraction unit
410 Discernment processing unit
412 Determination unit
420 Learning processing unit

The invention claimed is:

1. A motor teaching system for detecting cerebral activity of a subject and supporting motor training of the subject, comprising:
an operation device configured to teach motion to the subject in accordance with a predetermined motor pattern by guiding movement of a movable part of a body of the subject;
a measurement device configured to acquire a cerebral activity signal, by measuring the cerebral activity of the subject; and
one or a plurality of computers configured to control an operation for teaching the motor pattern by the operation device and configured to classify the cerebral activity of the subject into one of a plurality of classes including a motor imagery class by decoding the cerebral activity signal,
wherein the one or the plurality of computers output whether the cerebral activity of the subject during a teaching period of the motor pattern is classified into the motor imagery class, as a result of decoding the cerebral activity signal acquired by the measurement device during the period in which the operation device is caused to execute the operation for teaching the motor pattern,
wherein the one or the plurality of computers hold information indicating a plurality of transition patterns of cerebral activity of the motor pattern from prior to teaching to during teaching,
wherein the one or the plurality of computers specify a transition pattern of the subject from the plurality of transition patterns,
wherein the one or the plurality of computers determine an evoking content to be performed to the subject prior to teaching of the motor pattern, such that the cerebral activity of the subject during the teaching period of the motor pattern is classified into the motor imagery class, based on the specified transition pattern of the subject,
wherein the one or the plurality of computers output the determined evoking content, prior to teaching of the motor pattern,
wherein the plurality of transition patterns of cerebral activity comprises the following four patterns:
(A) cerebral activity during the motor teaching period is in a motor imagery state when cerebral activity prior to motor teaching is in the motor imagery state; whereas cerebral activity during the motor teaching period is in a rest state when cerebral activity prior to motor teaching is in the rest state;

(B) cerebral activity during the motor teaching period is in the rest state when cerebral activity prior to motor teaching is in the motor imagery state; whereas cerebral activity during the motor teaching period will be in the motor imagery state when cerebral activity prior to motor teaching is in the rest state;

(C) cerebral activity during the motor teaching period is in the motor imagery state, irrespective of the class of cerebral activity prior to motor teaching; and (D) cerebral activity during the motor teaching period is in the rest state, irrespective of the class of cerebral activity prior to motor teaching.

2. The motor teaching system according to claim 1, wherein the one or the plurality of computers:
instruct the subject to evoke the evoking content, prior to teaching of the motor pattern, and
instruct the operation device to start the operation for teaching the motor pattern, in response to the cerebral activity of the subject being classified into a class corresponding to the evoking content, as a result of decoding the cerebral activity signal acquired prior to teaching of the motor pattern.

3. The motor teaching system according to claim 2, wherein the one or the plurality of computers:
cause the operation device to execute the operation for teaching the motor pattern, in response to the cerebral activity of the subject being classified into a class corresponding to the evoking content, as a result of decoding the cerebral activity signal acquired by the measurement device, after instructing the subject to evoke the evoking content,
change the evoking content for instructing to the subject, in a case where the cerebral activity of the subject is classified into a class other than the motor imagery class, as a result of decoding the cerebral activity signal acquired by the measurement device, during the teaching period of the motor pattern,
instruct the subject to evoke the changed evoking content, and
cause the operation device to again execute the operation for teaching the motor pattern, in response to the cerebral activity of the subject being classified into a class corresponding to the changed evoking content, as a result of decoding the cerebral activity signal acquired by the measurement device, after instructing evoke of the changed evoking content.

4. The motor teaching system according to claim 2, wherein the evoking content is one of a rest state and a motor imagery state.

5. The motor teaching system according to claim 1, wherein the one or the plurality of computers feed back the result of having classified the cerebral activity of the subject, prior to teaching of the motor pattern, and do not feed back the result of having classified the cerebral activity of the subject, during teaching of the motor pattern.

6. The motor teaching system according to claim 1, wherein the operation device is a force presentation device comprising a robotic arm.

7. The motor teaching system according to claim 1, wherein the operation device is an exoskeleton robot.

8. The motor teaching system according to claim 1, wherein the measurement device includes a wireless headset using a dry electrode.

9. A motor teaching method for detecting cerebral activity of a subject and supporting motor training of the subject, using a system including an operation device configured to teach motion to the subject in accordance with a predetermined motor pattern by guiding movement of a movable part of a body of the subject, a measurement device configured to acquire a cerebral activity signal, by measuring the cerebral activity of the subject, and one or a plurality of computational devices configured to hold information indicating transition patterns of cerebral activity of the motor pattern from prior to teaching to during teaching, the method comprising:
a step in which the one or the plurality of computational devices specify a transition pattern of the subject from the plurality of transition patterns;
a step in which the one or the plurality of computational devices determine an evoking content to be performed with respect to the subject prior to teaching of the motor pattern, such that the cerebral activity of the subject during the teaching period of the motor pattern is classified into a motor imagery class, based on the specified transition pattern of the subject;
a step in which the one or the plurality of computational devices instruct the subject to evoke the determined evoking content, prior to teaching of the motor pattern;
a step in which the one or the plurality of computational devices classify the cerebral activity of the subject into one of a plurality of classes including the motor imagery class, by decoding the cerebral activity signal acquired by the measurement device; and
a step in which the one or the plurality of computational devices cause the operation device to execute an operation for teaching the motor pattern, in response to the cerebral activity of the subject being classified into a class corresponding to the evoking content, as a result of decoding the cerebral activity signal acquired prior to teaching of the motor pattern,
wherein the plurality of transition patterns of cerebral activity comprises the following four patterns:

(A) cerebral activity during the motor teaching period is in a motor imagery state when cerebral activity prior to motor teaching is in the motor imagery state; whereas cerebral activity during the motor teaching period is in a rest state when cerebral activity prior to motor teaching is in the rest state;

(B) cerebral activity during the motor teaching period is in the rest state when cerebral activity prior to motor teaching is in the motor imagery state; whereas cerebral activity during the motor teaching period will be in the motor imagery state when cerebral activity prior to motor teaching is in the rest state;

(C) cerebral activity during the motor teaching period is in the motor imagery state, irrespective of the class of cerebral activity prior to motor teaching; and (D) cerebral activity during the motor teaching period is in the rest state, irrespective of the class of cerebral activity prior to motor teaching.

10. A computer comprising:
one or a plurality of computational devices; and
a storage device configured to hold a program that is executed by the one or the plurality of computational devices,
the one or the plurality of computational devices executing:
a step of acquiring, for each of a plurality of subjects, a spatial filter to be utilized in decoding cerebral activity of the subject, and a reproducibility of a predetermined motor pattern calculated based on a result of having performed motion reproduction of the motor pattern, after teaching the motor pattern using an operation device configured to teach motion in accordance with the motor pattern by guiding movement of a movable part of a body of the subject;
a step of classifying the spatial filters of the subjects into a plurality of groups, by clustering the spatial filters of the subjects;
a step of specifying, from the plurality of groups, an optimal group to which a spatial filter of a subject with a highest degree of mastery of the motor pattern belongs, based on the reproducibility of the motor patterns of the subjects,
a step of holding information indicating a plurality of transition patterns of cerebral activity of the motor pattern from prior to teaching to during teaching,
a step of specifying a transition pattern of the subject from the plurality of transition patterns,
a step of determining an evoking content to be performed to the subject prior to teaching of the motor pattern, such that the cerebral activity of the subject during the teaching period of the motor pattern is classified into the motor imagery class, based on the specified transition pattern of the subject, and
a step of outputting the determined evoking content, prior to teaching of the motor pattern,
wherein the plurality of transition patterns of cerebral activity comprises the following four patterns:
  (A) cerebral activity during the motor teaching period is in a motor imagery state when cerebral activity prior to motor teaching is in the motor imagery state; whereas cerebral activity during the motor teaching period is in a rest state when cerebral activity prior to motor teaching is in the rest state;
  (B) cerebral activity during the motor teaching period is in the rest state when cerebral activity prior to motor teaching is in the motor imagery state; whereas cerebral activity during the motor teaching period will be in the motor imagery state when cerebral activity prior to motor teaching is in the rest state;
  (C) cerebral activity during the motor teaching period is in the motor imagery state, irrespective of the class of cerebral activity prior to motor teaching; and
  (D) cerebral activity during the motor teaching period is in the rest state, irrespective of the class of cerebral activity prior to motor teaching.

11. A motor teaching system for detecting cerebral activity of a subject and supporting motor training of the subject, comprising:
an operation device configured to teach motion to the subject in accordance with a predetermined motor pattern by guiding movement of a movable part of a body of the subject;
a measurement device configured to acquire a cerebral activity signal, by measuring the cerebral activity of the subject; and
one or a plurality of computers configured to control an operation for teaching the motor pattern by the operation device and configured to classify the cerebral activity of the subject into one of a plurality of classes including a motor imagery class by decoding the cerebral activity signal,
wherein the one or the plurality of computers execute:
a first step of acquiring, for the subject, prior to teaching of the motor pattern by the operation device, a set of a cerebral activity signal from when the motor imagery is carried out and a cerebral activity signal from when imagery other than the motor imagery is carried out, as a training data set;
a second step of creating a spatial filter to be utilized in decoding the cerebral activity of the subject, based on the training data set;
a third step of determining whether the created spatial filter belongs to the optimal group specified as a group to which a spatial filter of a subject with a highest degree of mastery of the motor pattern belongs;
a fourth step of starting teaching of the motor pattern by the operation device, in a case where the created spatial filter belongs to the optimal group,
a fifth step of holding information indicating a plurality of transition patterns of cerebral activity of the motor pattern from prior to teaching to during teaching,
a sixth step of specifying a transition pattern of the subject from the plurality of transition patterns,
a seventh step of determining an evoking content to be performed to the subject prior to teaching of the motor pattern, such that the cerebral activity of the subject during the teaching period of the motor pattern is classified into the motor imagery class, based on the specified transition pattern of the subject, and
an eighth step of outputting the determined evoking content, prior to teaching of the motor pattern,
wherein the plurality of transition patterns of cerebral activity comprises the following four patterns:
  (A) cerebral activity during the motor teaching period is in a motor imagery state when cerebral activity prior to motor teaching is in the motor imagery state; whereas cerebral activity during the motor teaching period is in a rest state when cerebral activity prior to motor teaching is in the rest state;
  (B) cerebral activity during the motor teaching period is in the rest state when cerebral activity prior to motor teaching is in the motor imagery state; whereas cerebral activity during the motor teaching period will be in the motor imagery state when cerebral activity prior to motor teaching is in the rest state;
  (C) cerebral activity during the motor teaching period is in the motor imagery state, irrespective of the class of cerebral activity prior to motor teaching; and
  (D) cerebral activity during the motor teaching period is in the rest state, irrespective of the class of cerebral activity prior to motor teaching.

12. The motor teaching system according to claim 11, wherein the one or the plurality of computers again execute the first step, the second step and the third step, in a case where the created spatial filter does not belong to the optimal group.

13. The motor teaching system according to claim 11, wherein a recommended class in which cerebral activity recommended during the teaching period of the motor pattern is associated with the optimal group, and the one or the plurality of computers output the evoking content to be performed to the subject prior to teaching of the motor pattern, such that the cerebral activity of the subject during the teaching period of the motor pattern is classified into the recommended class associated with the optimal group.

* * * * *